(12) United States Patent  
Casana-Giner et al.

(10) Patent No.: US 8,685,446 B2  
(45) Date of Patent: Apr. 1, 2014

(54) CONTINUOUS MULTI-MICROENCAPSULATION PROCESS FOR IMPROVING THE STABILITY AND STORAGE LIFE OF BIOLOGICALLY ACTIVE INGREDIENTS

(76) Inventors: Victor Casana-Giner, Ebenfurth (AT); Miguel Gimeno-Sierra, Berndorf (AT); Barbara Gimeno-Sierra, Berndorf (AT); Martha Moser, Puchberg am Schneeberg (AT)

( * ) Notice: Subject to any disclaimer, the term of this patent is extended or adjusted under 35 U.S.C. 154(b) by 289 days.

(21) Appl. No.: 12/885,165

(22) Filed: Sep. 17, 2010

(65) Prior Publication Data

US 2011/0064778 A1    Mar. 17, 2011

Related U.S. Application Data

(62) Division of application No. 10/596,556, filed as application No. PCT/ES2004/000562 on Dec. 17, 2004, now Pat. No. 8,168,225.

(51) Int. Cl.  
*A61K 9/16* (2006.01)

(52) U.S. Cl.  
USPC ........... 424/463; 424/451; 424/452; 424/458; 424/490

(58) Field of Classification Search  
USPC .......................... 424/464–489, 451, 452, 458  
See application file for complete search history.

(56) References Cited

U.S. PATENT DOCUMENTS

| 3,875,074 A | 4/1975 | Vassiliades et al. |
| 4,308,165 A | 12/1981 | Vassiliades et al. |
| 5,277,979 A * | 1/1994 | Kielbania et al. ........ 428/402.21 |
| 2003/0044490 A1 * | 3/2003 | Qi et al. ........................ 426/98 |
| 2004/0023894 A1 * | 2/2004 | Hasler-Nguyen et al. ...... 514/27 |

FOREIGN PATENT DOCUMENTS

| DE | 3920679 | 1/1991 |
| EP | 1344516 | 9/2003 |
| ES | 2066044 | 3/1995 |
| WO | 2005058476 | 6/2005 |

OTHER PUBLICATIONS

International Search Report issued in connection with International Application No. PCT/ES2004/000562, completed Mar. 15, 2005, mailed Apr. 5, 2005, 4 pages.

\* cited by examiner

*Primary Examiner* — Michael G Hartley  
*Assistant Examiner* — Micah-Paul Young  
(74) *Attorney, Agent, or Firm* — Vedder Price PC

(57) ABSTRACT

The invention relates to microcapsules, and a continuous micro-encapsulation water-in-oil-in-water microencapsulation process through in situ and interfacial polymerization of the emulsion. The formulation comprises a continuous water phase having a dispersion of microcapsules which contain oil drops and wherein the inside of each oil phase drop—containing optionally oil-soluble materials—there is a dispersion of water, or aqueous extract or water dispersible material or water soluble material. The oil drops are encapsulated with a polymerisable material of natural origin. Such microcapsules are appropriated for spray-dry processes, to be used as dry powder, lyophilised, self-emulsifiable powder, gel, cream and any liquid form. The active compounds included in the microcapsules are beneficial to the health and other biological purposes. Such formulations are appropriate to be incorporated in any class of food, especially for the production of nutraceuticals, as well as cosmetic products (such as rejuvenescence creams, anti-wrinkle creams, gels, bath and shower consumable products and sprays). The preparations are adequate to stabilise compounds added to the food, media for cultivating microbes and nutraceuticals, especially those which are easily degradable or oxidizable.

16 Claims, 17 Drawing Sheets

Fig. 7
7a
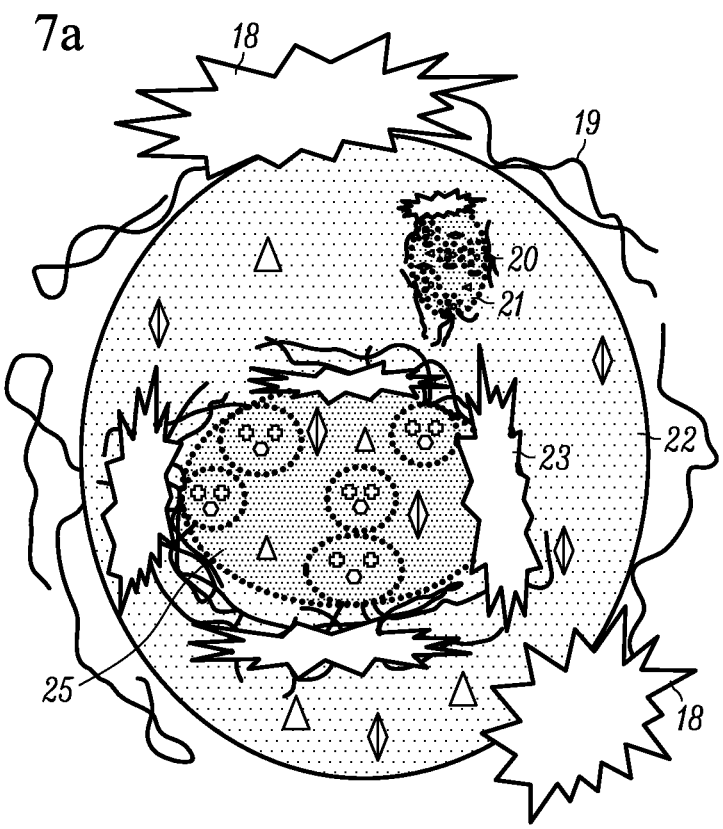
7b
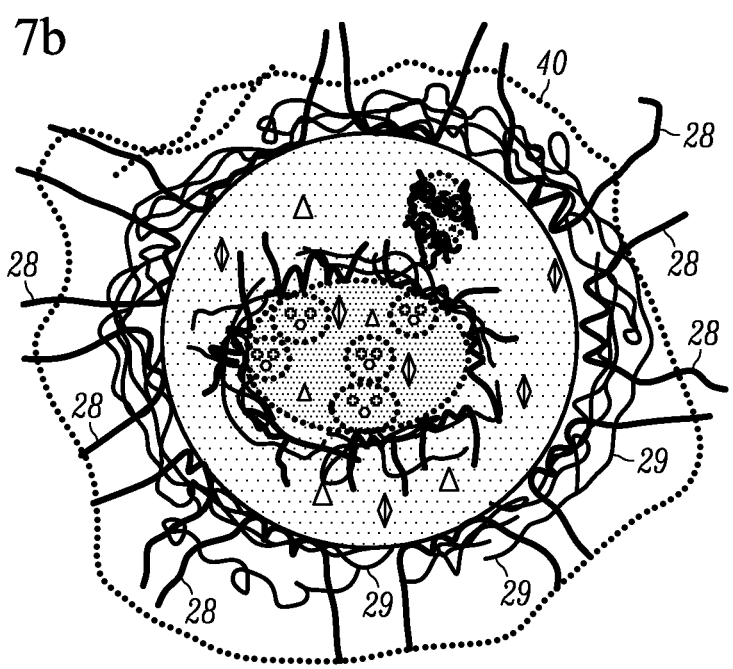

CONTINUOUS MULTI-MICROENCAPSULATION PROCESS FOR IMPROVING THE STABILITY AND STORAGE LIFE OF BIOLOGICALLY ACTIVE INGREDIENTS

CROSS REFERENCE TO RELATED APPLICATIONS

This application is a divisional of and claims priority from application Ser. No. 10/596,556, filed Jun. 16, 2006, entitled "CONTINUOUS MULTI-MICROENCAPSULATION PROCESS FOR IMPROVING THE STABILITY AND STORAGE LIFE OF BIOLOGICALLY ACTIVE INGREDIENTS"; which claims priority to PCT/ES04/00562, filed Dec. 17, 2005, which are both expressly incorporated by reference herein.

DESCRIPTION

Notes:
Use of Special Terminology:
An expression than contains "A, B and/or C" means that permits the combinations A, A+B, B, C, A+C, B+C, A+B+C and its permutations.

ABBREVIATIONS

The following list consists in terms commonly employed in the field of the invention:
W=water
O=oil
W/O=emulsion water in oil
O/W=emulsion oil in water
(W/O)/W=emulsion water in oil in water
a.i.=active ingredient(s). In the present invention it means biologically active ingredient(s), except when it is evident from the text that the ingredients are used not for biological functions. The use of singular or plural it is deduced from the text
UV=ultraviolet light
FA=fatty acid, with a carbon chain of more than 6 carbons
FA=saturated fatty acid
MUFA=monounsaturated fatty acid (1 unsaturated bond)
PUFA=polyunsaturated fatty acid (2 or more unsaturated bonds)
HUFA=highly polyunsaturated fatty acid (4 or more unsaturated bonds)
w-3=UFA omega-3, it is said, that contains at least an unsaturation in the third carbon when numbering the chain beginning from the opposite side of the carboxylic group
w-6=UFA omega-6, defined as w-3, except in that the first unsaturation (at least one) when numbering the chain beginning from the opposite side of the carboxylic group, is in position 6 instead of 3.
The abbreviations w-3 and w-6 are referred either to the singular or plural case; FA, SFA, UFA, MUFA, PUFA, HUFA may be ended in "s" (e.g. HUFAs) when they are referred to plural case.
GMOs=Genetically modified organisms
The invention relates to microcapsules, and a continuous micro-encapsulation water-in-oil-in-water microencapsulation process through in situ and interfacial polymerization of the emulsion. The formulation comprises a continuous water phase having a dispersion of microcapsules which contain oil drops and wherein the inside of each oil phase drop—containing optionally oil-soluble materials—there is a dispersion of water, or aqueous extract or water dispersible material or water soluble material. The oil drops are encapsulated with a polymerisable material of natural origin. Such microcapsules are appropriated for spray-dry processes, to be used as dry powder, lyophilised, self-emulsifiable powder, gel, cream and any liquid form. The active compounds included in the microcapsules are beneficial to the health and other biological purposes. Such formulations are appropriate to be incorporated in any class of food, especially for the production of nutraceuticals, as well as cosmetic products (such as rejuvenescence creams, anti-wrinkle creams, gels, bath and shower consumable products and sprays). The preparations are adequate to stabilise compounds added to the food, media for cultivating microbes and nutraceuticals, especially those which are easily degradable or oxidable.

FIELD OF THE INVENTION

The field of the invention corresponds to methods of formulation, use of biologically active materials, specially in foodstuffs, more specially in nutraceuticals of functional foods, comprises method of microencapsulation, microcapsules produced thereof and application (use) of them when they include certain compounds, some of them described in this document for the first time.

STATE OF THE ART

Microencapsulation
The microencapsulation technique is known and used in many fields (pharmacy, agrochemistry, dyestuffs, etc). There exist different forms to microencapsulate compounds in such a way they are controlled released. For a thorough and correct definition of the term microcapsule, and a broad prior art, check Fong, M. "Technologies of microencapsulation" in "Controlled Release Systems: Fabrication Technology, 1988 Vol I, Editor Dean Hsieh, CRD Press, Florida. There is explained that often is confounded the term "microcapsule" must not be confounded with other formulation methods as emulsions, microspheres, liposomes, etc. "True" microcapsules (what we call microcapsules in this invention), are based in a physical separation of phases by means of a wall (polymer) that has inside—the "core"—the microencapsulated material. "True" microencapsulation (the one referred to in this invention) must be not confounded the technique of formulate materials by dispersing or mixing them in polymeric matrices (without a clear physical separation of phases). Care must be taken to avoid considering microcapsules as simple emulsions. There is a huge amount of literature (patents and scientific papers) regarding matrix encapsulation, as well as emulsions W/OW (water in oil in water), W/O (water in oil) and O/W (oil in water). A fundamental differentiation of the present invention with all the previous patents referring to true microcapsules (hereinafter, microcapsules) is that we create an emulsion W/O that is enclosed by a microcapsule's wall, and these microcapsules are dispersed or emulsified in water, moreover, the microcapsules can contain smaller microcapsules in the core, thus having multi-microcapsules. On one side, the microcapsules here disclosed (and their production method) are characterized in that the wall is made of a mix of hydrocolloids that are polymerized and cross-linked and the hardening of the structure is due to an increase in temperature, the process runs without time laps in between process steps and under continuous agitation. No patent or scientific paper discloses a microencapsulation method similar to this one.

No patent or scientific paper discloses a microencapsulation method similar to ours. The closest state of the art regarding this invention is represented by U.S. Pat. No. 6,234,464.

U.S. Pat. No. 6,234,464 describes a method of microencapsulation of FA (Fatty Acids). Differences with respect the present invention are: i) in U.S. Pat. No. 6,234,464 the core of the microcapsule has only an O (oil) phase; in our invention the core has a W/O phase ii) in U.S. Pat. No. 6,234,464 the core contains no multi-microencapsulated drops; in our invention the core contains (as statistically distributed) microcapsules inside of the core of bigger microcapsules iii) in U.S. Pat. No. 6,234,464 the wall is limited to two hydrocolloids, further separated and differentiated into two layers; in our invention is possible and convenient to combine more than two hydrocolloids and there is no differentiated layered structure iv) in U.S. Pat. No. 6,234,464, during the process disclosed in example 1, the process includes a pH change step and a cooling step to harden the microcapsules; in our invention, hardening is done by increase of temperature at the end of a continuous process, because there is no need to form a "first layer" and later a "second layer" (we allow all the hydrocolloids to polymerize and cross-link together) v) in U.S. Pat. No. 6,234,464 are not in contact with any other compound; in our invention it is recommendable that either in the oil phase or in any of the two water phases, stabilizers and antioxidants are used vi) the hardening step done in U.S. Pat. No. 6,234,464 is by done means of cooling; while we use increase of temperature, and in our case the wall is strenhgher vii) in U.S. Pat. No. 6,234,464 for obtaining dry microcapsules and remove water from the walls, it is used ethanol; in our invention it can be obtained dried microcapsules (in powder form) without the use of ethanol.

Although the differences mentioned are many, they make reference to the process; the microcapsules formed thereof also present rather different characteristics, in particular regarding thermal properties, controlled release of active ingredients (U.S. Pat. No. 6,234,464 refers only to FA), etc. Any other disclosed process of microencapsulation and microcapsules produced thereof differ from our invention even more than U.S. Pat. No. 6,234,464.

Use of FA in Foodstuffs

It is known for the skilled in the art that certain UFAs are healthy, in particular MUFAs, PUFAs and HUFAs. We can differentiate w-3 and w-6. Following publications of scientist and epidemiological studies many patents have been filed afterwards, that, based on such studies, that claim the use of these natural compounds, that have been consumed by the humankind since its beginning The inventors of this patent do not know any patent that claims the combined use of FA with sphingolipids either with cerebrosides.

The methods of application of all these compounds are widely varied, including microencapsulation but not even similar to the one herein described (that is characterized in that allows to incorporate to any kind of foodstuff microencapsulated UFAs without a significant degradation of them).

It is described the combination of UFAs with antioxidants (EP 404058, U.S. Pat. No. 5,855,944) but in no case are used microcapsules as those described herein, and lack any sound research on the quality of the UFAs one the foodstuff is industrially processed (namely, no degradation of UFAs), or just the shelf-life stability.

There exist many sources of UFAs, practically all of them described in scientific papers before being claimed in patents. The novelty of this patent is not referred to the sources of the UFAs, rather in the microencapsulation of UFAs obtained from natural sources (or GMOs), or by organic syntheses, in microcapsules for its use in foodstuffs and other uses.

Infant Foods

A particular embodiment of this invention is the use of our formulation in infant foods. Cow's milk lacks of certain UFAs that are present in the mother's milk. This type of nutritional complementation has been elsewhere claimed, but no such disclosure has been made with regard of microencapsulated materials and the optimal conservation of the UFAs till final consume (WO 9213086).

Intelligence Development

It is a nowadays debate the increase of intelligence, or at least the potential intelligence, by DNA recombinant techniques. The inventors, based in diverse scientific papers that describe the development of the brain cortex (where the intelligence resides) with a correct and balanced consume of UFAs w-3, w-6 and w-9, as well as the role of certain sphingolipids in neuronal transmissions, and knowing human metabolic pathways, have found a solution for a new demand of the society: to develop to the maximum extent the potential of the human, in particular the intelligence, as the distinctive feature of the humankind, by addition of certain natural compounds to the diet. We describe here the combined use of w-3, w-6 and w-9 and sphingolipids, in particular cerebrosides to increase the potential development of the intelligence, The inventors are not aware of such use of compounds for the aforementioned purpose, lesser in the form of microencapsulated material, and much lesser in microcapsules as herein described. There is already scientific evidence for the use of w-3 and w-6 and w-9 in regard intelligence (but not combined with sphingolipids or cerebrosides for brain development). See Biol. Neonate 1998, 74:416-429 and "Evidence for the unique function of DHA during evolution of the modern hominid brain", Lipids 1999, vol. 34(S):S39-S47. The latter points out to the role of DHA in the development of intelligence from hominids to humans.

Use of antioxidants, protectors and blockers of UV-light, and free-radical blockers.

It is well known that the origin of many illnesses, from cancer till cataracts is due to oxidation reactions, degradation of DNA chains due to oxidation processes and induced by oxidants, UV-light and or free radicals. Many inventions relate to the use of natural antioxidant extracts, antioxidant compounds, etc (EP 1344516, EP 1064910) to prevent a wide array of diseases. However, the present invention achieves the needed fact that the antioxidant compounds or extracts preserve their antioxidant capacity through industrial processes and strong stressing environments, until the consumer gets the compounds in a perfect quality and functional state (not degraded), thanks to our microencapsulation technology.

DETAILED DESCRIPTION OF THE INVENTION

We refer to a continuous multi-microencapsulation process, and microcapsules thereof and their uses, by means of in situ interfacial polymerization of biologically active materials characterized in that, (a) in a first step it is added to an oil phase [that contains optionally at least a biologically active material] a water phase containing a polymerization initiator and optionally, at least a biologically active material; further exists at least one surfactant in at least one of the two mentioned phases, and there exists a biologically active material in at least one of the two phases, (b) In a second step, it is added [to (a)] a solution or dispersion in water that contains at least one hydrocolloid, this producing a phase inversion and the hydrocolloid begins to be deposited and polymerized on the walls of the new formed drops [consisting in a water in oil emulsion], occurring also a cross-linking of the hydrocolloid polymers, optionally in the presence of cations, (c) In a third step, it is added [to (b)] a solution or dispersion in water that contains at least one protective colloid, that begins to be deposited on the surface of the drops of water in oil, and to polymerize and cross-link with itself and the hydrocolloid, (d) In a fourth step, it is added [to (c)] a solution or dispersion in water of a primary surfactant that allows a reduction of the size of the water in oil drops, (e) In a fifth step, during the process of reduction of size, the partially formed microcapsules are deaglomerated and reaglomerated, happening eventually an enclosure of drops inside bigger drops (multi-microencapsulation), (f) When enough time has passed in order that the oil [water in oil] drops are covered by at least one hydrocolloid and at least a protective colloid, the temperature is increased in order to strengthen the wall of the mentioned drops; at this time the drops are already microcapsules or multi-microcapsules suspended in water.

(g) Optionally, the formulation is dried for obtaining dust, optionally it is reformulated by means of state of the art techniques to obtain (or to mix the microcapsules with) wettable powders, gels, cosmetic creams or medicinal, bath products, microorganism media; optionally additives are added (optionally antiagglomerating agents) for microcapsules' dried formulations.

(h) All the process—except optionally step (g)—is carried out under continuous agitation.

In a more detailed description of the process, referred to the Figures, that is an alternative description with the same subject matter, and referring to the drawings we refer to a process for the preparation of microcapsules characterized in that:

(a) Two different solutions (FIG. 1) $1a$ (oil) and $1b$ (water) are mixed by addition of $1b$ to $1a$, these solutions containing active ingredients and optionally free or sequestered cations to be liberated later, (b) Thanks to a food emulsifier that can be in $1a$ or in $1b$, an emulsion of water drops (10) into the oil phase (9) is formed. This step is finished with the formation of emulsion $1c$, where in the oil phase (9) are solubilized or dispersed—preferably liposoluble—active ingredients; it is also formed an oil in water emulsion, with the water droplets (10) containing—preferably hydrosoluble—active ingredients, being optional that the solubility [of the active ingredients] in water or in oil is modified by derivatization of the active ingredient(s), (c) Then, it is added to existing emulsion [$1c$] the solution $2b$, having $2b$ at least one hydrocolloid [able to be polymerized and cross-linked] and optionally containing at least one active ingredient, (d) It follows a phase inversion, having then dispersed drops (11) that are an emulsion of water (12) in oil, dispersed in the continuous phase (24), namely, water, (e) Later, (FIG. 5) it is added a solution or dispersion $5a$, containing at least a hydrocolloid (15) that acts as protective colloid, The solution or dispersion containing the primary emulsifier is added to emulsion $2a$.

(f) when the polymerization and cross-linking reactions are deemed to be finalized, reaching a reduction of particle size to about 1-30 m, the temperature that remained at about 30-70° C. is raised to 60-100° C.

(g) Finally it is added a food grade viscosity modifier.

(h) Optionally, the formulation may be spray-dried or any state of the art technique, and to be collected to form dry powders, self-emulsifiable powders, gels, creams or any other form that may contain them, including oil dispersions, as well as to be submitted to a lyophyllization unit operation.

We also refer to process of microencapsulation of biologically active materials

PREFERRED EMBODIMENT OF THE INVENTION

Since the preferred embodiment is the use of the microcapsules to add to functional foods, the microcapsules have been submitted to tests against thermal, pressure and pH in specific ranges degradation.

The hydrocolloid(s) as well as the protective colloid(s) may be added together in the form of a solution or aqueous dispersing initially.

The primary emulsifier and the protective colloid can be chosen in between the group of hydrocolloids, as well as the viscosity modifier, because the hydrocolloids posses all these features.

The group of compounds more adequate for a successful formulation (functionally acceptable, it is said, it serves for a functionally acceptable encapsulation of biologically active ingredients and also to other living or mineral materials, in the way that functionally acceptable is understood as industrially usable for the purposes for what the materials have been microencapsulated, each functionality is highly dependant in the final use) according the described process corresponds to chitosans, starches, dextrins, cyclodextrins, celluloses, lignines, pectines, agar alginates, carragenatos, gelatins, guar gum, Arabic gum, tragacanth, lignosulfonates, Caravan gum, *Ceratonia siliqua* gum, saponines, Xanthan gums, seeds' gums, galactomanans, arabanogalactomanans, beta-glucanes, inulin, Psyllium, acacia gum, in all their isomeric and stereochemical configurations, in all their variations regarding quantity and quality of monomers or oligomers that constitute the hydrocolloid, in all their presentation forms, as metal, nitrogenated, phosphorated, sulfurated salts, as well all the derivatized products of the referred hydrocolloids.

The hydrophylic-lipophylic value (HLB) of the primary emulsifier can be conveniently chosen in between 9 and 16, preferably in between 12 and 14.

The emulsion $1c$ (10) typically has a particle size (a Master Sizer® laser equipment is referred for all particle size measurements) of 50-500 µm, preferably 70-200 µm.

At the end of the process, the formed microcapsules have a size of 0.1-100 µm, preferably in the range 1-30 µm, more preferably 1-5 µm. This size may vary with time with aggregation processes that in to some extent may be desirable as far as the total structure of the formulation is not affected.

The shear stress to reduce the particle size of the emulsion and normal agitation is given by state of the art agitators (anchor, teeth, combinations) and by an approximate speed of 3000 to 25000 rpm. These values depend on the stage of the process and the dimension of reactors. Once the microcapsules are formed is not recommended to provide too much kinetic/thermal energy, in order to avoid microcapsules' destruction.

Particular types of colloids are the hydrogels, and then the hydrocolloids may be substituted by hydrogels optionally based in albumin, alginates, policarboxylates, poli-L-lactid, starch and derivatives. We can choose, according the experimentally measured release rate (influenced by the media, e.g., yogurt) different combinations of hydrocolloids, changing the degree of polymerization, the hardness of the wall, the thickness of the wall and permeability (to determined type of materials) and electric properties.

This variability of the wall forming materials is also applicable to the viscosity modifiers and emulsifiers either the one(s) used to form (1c), preferably a polysorbate) as a primary emulsifier (preferably a soy lecitin based emulsifier).

The microcapsules may be obtained in a dry state, or to be redispersed in liquid phases or solid and solidifiable matrices. The outer media of the microcapsules may have compounds that help to maintain the wall structure, like ionic force regulators, osmotic pressure, etc. It is possible that inside the microcapsules there are present metallic cations that once formed, help in maintaining the structure, like Calcium ions inside a microcapsule's wall made with pectins.

The active ingredients may be added in any step of the process, including the phase of the process when the foodstuff is mixed with the microcapsules, but, obviously, is preferred that the materials are incorporated inside the microcapsules. Then, the active ingredients may come from solutions 1a, 1b, 2b, 5a or be added in any step of the final food process, when the microcapsules are previewed to be used in foodstuffs, that is a preferred embodiment of the invention (functional foods).

It is important to prevent oxidation processes (e.g., for UFAs and antioxidants). Then, the process may be conveniently performed under vacuum, in the presence of an inert gas (nitrogen, helium), protected from light of any wavelength and in sterile conditions.

We refer to water phase in this document to solutions or dispersions—apart form water alone—to those: (i) based in aqueous extracts (ii) with a content in alcohols lower than 40% being the rest water (iii) compounds soluble or dispersible in water (better explained, polar substances).

It must also understood that the oil phase is referred to any hydrophobic phase that is functionally acceptable (it leads to stable formulations, able to be incorporated in foodstuffs or used for other specific applications achieving the expected success), as it can be honey or waxes.

It must be also considered that the thermal properties of the water or oil phase may be modified to decrease the thermal stress inside and outside of the microcapsules, by virtue of the different thermal properties of water, alcohols or oils, as well as the transmission coefficients form phase to phase. The accumulation of thermal energy by the solutions and dispersions inside and outside of the microcapsules may be used to protect the active ingredients from deterioration. It can be added food grade microbiological stabilizers.

One embodiment of the invention refers to dry microcapsules covered by a microbiological stabilizers. For certain applications, particularly cosmetic ones, once the microcapsules are dry (or even in wet form) they can be added in gels, oils, alcoholic solutions for perfumes, etc. In an embodiment of the invention, the microcapsules contain flavours (aromas) to be used in perfumery or to provide perfumes to gels and bath creams or soaps.

The microcapsules can be applied to all type of foods, in a non restrictive way the following examples: cereals and derived (optionally muesli, cereals for milk), pastry shop, dairy products, nutritional supplements, sugars and derived (optionally chocolates, sweet, nougats, marzipans), sweet dietary (with low level of calories), in regime foods and for diabetics, oils and derived, milky and derived, eggs, vegetables and vegetables, vegetables, fruits, tubers and derived, eatable shafts, snacks, appetizers, eatable roots (optionally licorice), bay and wild products, preserves of fruits, dry fruits, meats, sausages, fish, shellfish and crustaceans and their preserves, alcoholic and not alcoholic drinks, carbonated drinks or not carbonated, juices, syrups, nectars, spices, condiments, pre-cooked foods, pre-processed foods (frozen mass of bread), pizzas, honey.

Although the main and more useful embodiment of the invention refers to feeding (of human and other animals, even fish and also microorganisms), the microcapsules can be employees for other purposes, in particular to encapsulate semiochemicals, attractants, repellent, insecticides, sterilizers, herbicides, fungicides, germicides, viricides (or materials that prevent the viral infections), vectors of genes (for gene therapy or for objectives of technical of recombinant DNA), aromas, indicatives of presence of compounds—as mixed in gas or liquids—, toilet chemicals, astringents to avoid the ingestion of toxic products also in household products. The invention can be carried out to avoid aromas, with the adaptation of the materials of the wall and other factors, in order to avoiding to the maximum the liberation of the encapsulated materials. This is especially useful for products enriched with omega-3/-6/-9 coming from fish oils, in such a way that the non-desirable scents are reduced to the minimum.

In an example presented later on, we will see that the applicant has used advanced statistical techniques usual to reduce the number of necessary tests to determine the most appropriate parameters to encapsulate certain compounds, or to obtain the speed of wanted liberation, etc. to select the independent variables: type of made up of the wall, particle size, emulsifiers(s), speed of rotation of the agitator, agitator type, modifier of viscosity, etc. and an independent variable that represents the quality of the formulation or of the microcapsules. This type of reduction of trials to reproduce the invention is recommended due to the high number factors involved in the repetition of the invention. It has been used the variance analysis or multiple variance analysis with design of factorial fractions, preferably factorial in 2, 4, 8, 16, 32, and 64 blocks, half saturated fraction, I design Box-Behnken, central compound, Plackett-Burman. The present invention is the five year-old result with more than 50,000 different formulations, however, without the employment of these statistical techniques, the number of rehearsals would ascend to, at least, a bigger number in 10 orders of magnitude.

Defining an aspect of the invention we can refer to the microcapsules taken place by means of a continuous process of multi-microencapsulation characterized because (a) they contain beneficial active ingredients for the human health; (b) the wall of the microcapsules is composed of a mixture of at least two hydrocolloids, such a mixture polymerized and cross-linked, such hydrocolloids are eatable: (c) the polymerization degree, cross-linking and nature of the hydrocolloids influence the controlled liberation of the active compounds and the protection against the oxygen and/or light and/or temperature; (d) the microcapsules contains in their interior an emulsion of water in oil, existing active ingredients optionally in the phase oils, optionally in the phase it dilutes or optionally in both phases and also, (e) they can contain smaller microcapsules (multi-microencapsulation possible until, at least, 5 degrees of multi-encapsulation); and the particle size of the microcapsules is in the range 0.1 μm-100 μm, preferably in the range 1 μm-10 μm (f) they are produced by means of a continuous process of multi-microencapsulation for polymerization interfacial in situ.

The microcapsules formed according to the process described, can liberate their content for reasons of at least an elected factor of the group of: pH, temperature, pressure, ionic force, osmosis, volatilization, presence of compounds that dissolve the wall of the microcapsule.

The formed microcapsules, in an embodiment corresponding to human consumption, they should resist the usual alimentary industry processes, in particular to operations, belonging to the state of the technique, concerning to protection against microorganisms, noxious and/or unwanted compounds presence, microorganisms settlers of the formulation or food to which is dedicated, and the invention provides microcapsules able to be submitted to unit operations like: sterilization, stabilization of microorganisms, pasteurization, UHT, ozonization, UV and gamma ray treatments, sterilizing irradiations.

In another embodiment, the formulation is accompanied with a certificate of quality where the nonexistence of heavy metals is analyzed, noxious products of degradation of the biologically active materials, agrochemical products used in the production of the compound biologically active and other materials that are noxious for the health.

In another embodiment of the invention, the microcapsules are used to provide nutritive anabolites, compounds that help to identify causing microbes of illnesses (as selective anabolites or radio-active fluorescent or marked products), and these compounds optionally can be liberated by pH changes in the means of cultivation (p. e.g., agar potato-dextrose), for production of enzymes (of the same microbial cultivation, p.ej.) or other metabolites (as alcohol or liberated enzymes).

The microcapsules can be added to natural or artificial sweeteners, salt, pepper, spices and condiments in general, in such a way that the addition of the mentioned condiments to the foods makes that the nutritious value is increased, or the benefit for the health of the foods.

For a bigger protection of the wall of the same microcápsula, or the contained active compounds in it, it is convenient to include compound(s) inside or outside of the microcapsule that prevent the oxidative action of the ultraviolet rays.

A favorite embodiment is that in the one that the material to be microencapsulated are compounds that are known by the scientists and for the public as very appropriate to maintain the health or to prevent illnesses, or even to cure illnesses. Nevertheless, when considering the number of patents that claim the use of certain compounds (antioxidants and acids fatty omega-3, omega-6 and w-9 mainly), it is necessary to have present that the an overwhelming percentage, these patents have been requested after the beneficial effects of these compounds were described by the scientific community in articles and conferences. It is then, the objective of our invention, to apply well-known compounds as healthy in microencapsulated form since our microencapsulation method is able to maintain until the final consumption by the consumer or of any other animal, all the beneficial properties of the active compounds (to avoid its degradation). The practical entirety of products which are described in this patent, have been described as beneficial for more than 20 years, or even used consciously by the humanity or unconsciously for its benefits for millennia, and even from the origins of the mankind In this sense, the inventors choose the non-limiting group of compounds, (in combinations or partially or used individually), to be microencapsulated as the following: green tea, black tea, cocoa, red wines or red grapes or residues of grapes (pomaces and marcs), cider or apple or apple juice, germ or saved of cereals, carrots, chili, garlic, radish (especially, spicy radish), as a for long time used foodstuffs.

In the same way it has been already explained, the present invention allows the formulation of a variety of material types, being novel that the microencapsulated materials are microencapsulated with edible materials, and protect from degradation in the industrial processes or the kitchen, in a much higher degree than what is prior art, thanks to the structure of the multi-microcapsule. After the high number of experiments performed by the inventors, and considering that the chemically similar compounds behave similarly in the process and in the microcapsule (e.g., pineno and limonene, being both monoterpenos, must present no difference at the time of microencapsulation either at the time of their release, even copaene, that is a sesquiterpeno, won't differ much from the monoterpenos, either limonene oxide, with an additional functional group, because fictional groups does not affect the formation of the microcapsule, either in the emulsion formation in a drastic way. In those cases where compounds may affect to the process as the need of special emulsifiers, the inventors have foreseen for cases, where different emulsifiers, polymers, etc. are used, and limited to those already mentioned—but able to overcome any difficulty in the process of encapsulating the following compounds or materials):

(a) Flavonoids in general and derivatives: anthocyianidins, pro-anthocyanidins, oligomer-procyanidine, isoflavones, chalcones, catechin, epihatechin, epicatechin gallate, epigallocatechin, epigallocatechin gallate, eriocitrin, narirutin, rutin, naringin, myricitrin, hesperidin, myricetin, eriodictyol, fisetin, quercetin, naringenin, luteolin, hesperidin, kaempferol, isorhamnetin, apigenin, rhamnetin, galangin, quercitrin, quercetin, diosmetin, taxifolin, galandin, biochanin A, genistein, eriodictyol, chrysin, hydroxytyrosol, oleuropein, gabardine, licochalcone, daidzein, matairesinol, secoisolariciresinol, enterodiol, enterolactone, equol, desmethylangolensin, luteoferol, luteolinidin, apiferol, apigenidin, leucocyanidin, taxifolin, pelargonidin; and derivatives thereof;

(b) phenolic acids in general and derivatives (preferably esters, glycosides, rutinosides and amines): gallic, sinapic, syringic, caffeic, chlorogenic, ferulic, (o-, m- or p-) coumaric, guaiacol, (o-, m- or p-) cresol, 4-ethylphenol, 4-vinylguaicol, eugenol, p-hydroxybenzoic, procatechuic, vanillic, hydroxycinnamic, tanins in general tannins, ellagiotannins, gallotannins; and derivatives thereof;

(c) esctructurally combined amides comprising hydroxycinnamic acids and anthranilic acids (avenanthramides), avenasterol, hydroxycinnamic acids and long-chain fatty acids or alcohols—and derivatives thereof—; indoleamines (e.g. melatonin); inulin, glutation;

(d) terpenoids in general and derivatives, monoterpenes, diterpenes, sesquiterpenes, triterpenes, tetraterpenes including the carotenoids: alfa-carotene, phytoene, cyclo-artenol, beta-carotene, ionone, zeaxanthin, capsanthin, astaxanthin, canthaxantin, violaxanthin, mutatoxanthin, luteoxanthin, auroxanthin, neoxanthin, apo-carotinal, xanthophylls; and derivatives thereof;

(e) commonly synthesized antioxidants for its use in foodstuffs and derivatives of the type of butylhydroxyanisol, 2,6-di-tert-butylhydroxytoluene, tert-butylhydroquinone, 2,6-di-tert-butylhydroquinone, 2,6-diterbutyl-4-hydroxymethylphenol, 2,4,5-trihydroxibutyrophenone; and derivatives thereof, tocopherols (e.g. alpha, beta, gamma and delta tocopherols—and derivatives thereof—; Tocotrienols (alpha, beta, gamma and delta tocotrienols—and derivatives thereof—); Tocochromanols;

(f) alpha-lipoic acid; coenzime Q-10; vitamins; aminoacids (preferably L-arginine, cistina and cisteine) and their corresponding organic polymers like oligopeptides, peptides—preferably carnosine, carnitine, glutathion—; enzymes; enzyme inhibitors (preferably phenolases or oxigenases or lipooxigenasas or lipases inhibitors;

(g) minerals and oligoelements, especially those involved in redox processes in vivo like selenium, zinc, magnesium.

The natural sources where the above compounds (or other compounds not yet known or already known but not mentioned in the natural sources above) may be selected—considering state of the art methods of extraction of any interesting material (in pure or mixed form, in any physical state)—can be selected from accepted vegetal additives for its use in foodstuffs, considering additives something that is added to the foodstuff, being a predominant of fundamental part of the foodstuff or not. Some narcotic-producing plants are considered by the inventors able to be used in medicine. Finally, in the following list are listed plants with known therapeutic properties and used in herboristery and para-pharmacy. This is a list of non-limiting examples of natural a.i. to be microencapsulated, either by isolation of compounds, by aqueous or alcoholic solutions, also dispersions of leaves, roots, stems, flowers fruits, etc., grinded till certain suitable particle size, and also lyophilized preparations of such a.i. or preprocessed in any form. The list, in a non limiting sense is:

Medicago sativa, Pimenal officinalis, Hibiscus abelmoschus, Angelica archangelica, Galipea officinalis, Pimpinella anisum, Ferula foetida, Ferula asafetida, Melissa officinalis, Myroxylon pereirae, Ocimum basilicum, Pimenta acris, Citrus aurantium bergamia, Prunus amygdalus, Citrus aurantium, Citrus aurantium amara, Piper nigrum, Prunus spinosa, Aniba rosaeodora, Camelia oleifera, Camelia sinensis, Carum carvi, Elettaria cardamomum, Ceratonia siliqua, Daucus carota, Dacus carota sativa, Cascarilla, Apium graveolens, Anthemis nobilis, Matricaria chamomilla, Anthemis nobilis, Anthriscus cerefolium, Cichorium intybus, Cinnamomum spp., Cinnamomum zeylanicum, Cymbopogon nardus, Salvia sclarea, Trifolium pratense, Theobroma cacao, Coffea arabica, Coriandrium sativum, Cuminum cyminum, Taraxacum officinale, Sambucus nigra, Edelweiss, Helichrysum italicum, Foeniculum vulgare, Trigonella foenumgraecum, Arabidopsis spp., Zingiber officinale, Citrus grandis, Psidium guajava, Humulus lupus, Marrubium vulgare, Monarda punctata, Hyssopus officinals, Jasminum officinale, Jasminum grandiflorum, Juniperus spp. Juniperus comunis, Eucaliptus officinalis, Cola acuminata, Laurus nobilis, Lavandula spp. Lavandula hybrida, Taxus baccata, Citrus medica limonum, Myristica fragans, Marjorana hortensis, Thymus spp., Thymus officinalis, Thymus mastichina, Ilex paraguarensis, Chamomilla recutita, Saccharum officinarum, Myristica fragans, Allium cepa, Citrus aurantium dulcis, Carum petroselinum, Mentha pulegium, Mentha piperita, Pimenta officinalis, Chimaphila umbellata, Punica granatum, Pelargonium spp., Pelargonium graveolens, Rosmarinus officinalis, Crocus sativus, Salvia spp., Salvia officinalis, Mentha spicata, Mentha viridis, Satureia hortensis, Satureja hortensis, Origanum majorana, Tamarindus indica, Citrus reticulata, Artemisia dracunculus, Thea sinensis, Thymus vulgaris, Polianthes tuberosa, Curcuma longa, Prunus serotina, Thymus serpillum, Satureja Montana, Cananga odorata, Curcuma zedoaria, Plantago major, Adansonia digitata, Ananas comosus, Artocarpus altilis, Carica papaya, Lycopersicon esculentum, Cephalophus spp., Vaccinium myrtillus, Thymus aragonensis, Thymus spp., Citrus aurantiifolia, Citrus paradisi, Cucumis melo, Cucurbita spp., Vitis spp., Vitis vinifera, Mangifera indica, Lamiaceae (Coleus, Hedeoma, Hyptis, Leonurus, Leucas, Lycopus, Marrubium, Mentha, Monarda, Perilla, Prunella, Salvia, Stachys, Teucrium, Thymus), Cannabis spp., Digitalis lanata, Adonis vernalis, Aesculus hippocastanum, Frazinus rhychophylla, Agrimonia supatoria, Rauvolfia sepentina, Andrographis paniculata, Areca catechu, Atropa belladonna, Berberis vulgaris, Ardisia japonica, Betula alba, Ananas comosus, Camellia sinensis, Cinnamomum camphora, Camptotheca acuminata, Potentilla fragarioides, Erythroxylum coca, Papaver somniferum, Colchicum autumnale, Claviceps purpurea, Digitalis purpurea, Digitalis lanata, Glaucium flavum, Papaver somniferum, Gossypium spp., Hyoscyamus niger, Camptotheca acuminata, Piper methysticum, Lobelia inflata, Crotalaria sessiliflora, Nicotiana tabacum, Physostigma venenosum, Ephedra sinica, Cinchona ledgeriana, Rhododendron molle, Datura spp., Taxus brevifolia, Strychnos nux-vomica, Stevia rebaudiana, Theobroma cacao, Valeriana officinalis, Pausinystalia yohimbe, Ephedra spp. Crataegus oxyacantha, Hamamelis virginiana, Hydrastis Canadensis, Hypericum perforatum, Potentilla erectra, Ledum palustre, Salvia officinalis, Chamomilla recutita, Arctostaphylos uva, Eucommia ulmoides, Mytilus galloprovincialis, Diplazium esculentum, Manihot utillissima, Sauropous androgynus, Terminalia arjuna, Iberis amara, Crataegus spp., Arbutus unedo, Cynara scolymus, Amaranthus caudates, Alchornea laxiflora, Alpinia officinarum, Xanthophyllomyces dendrorhous, Crataegus monogyna, Taxus yunnanensis, Bacopa monniera, Cistus albidus, Ocimum basilicum, Rosmarinus officinalis, Thymus vulgaris, Bixa orellana, Centella asiatica, Urtica dioica, Agrocybe aegerita, Crataegus laevigata, Satureja hortensis, Crocus sativus, Coccinia indica, Brugia malayi, Rubus spp., Silybum marianum, Cannabis spp., Cannabis sativa, Hypericum perforatum, Rhus coriaria, Olea europaea, Cyclopia intermedia, Ginkgo biloba, Lentinus lepideus, Pseudomonas putida, Sargassum micracanthum, Pinus radiata, Pinus spp., Phaseoulus mungo, Cicer arietinum, Vigna sinensis, Phaseolus aureus, Dolichos lablab, Cajanus cajan, Vicia faba, Dolichos biflorus, Phaseolus lunatus, Phaseolus aconitifolius, Pisum sativum, Psophocarpus tetragonolobus, Arachis hypoagea, Brassica spp., Brassica campestris, Brassica napus, Valeriana officinalis, Echinacea purpurea, Echinacea pallida, Echinacea angustifolia, Glcyrrhiza glabra, Seronea repens, Vaccinium macrocarpon, Tancetum parthenuum, Tancetum parthenuum, Vaccinium macrocarpon, cereals, seed fruits, silvestre bays, leguminosae, green tea, black tea and microorganisms able to produce long-chained unsaturated fatty acids.

Another issue that is a social concern in developed countries is the consum of probiotic organisms, understanding such organisms as those that by virtue of their metabolism or by its presence in the (foreign) organism protect against infections (specially Candidasis), reduce cholesterol and glycerides levels and help digestion and intestinal movement. Usually these organisms are introduced in yogurts and other dairy products, but with our invention we are able to encapsulate living bacteria, yeasts and molds present in the so-called probiotic foodstuffs, and remaining alive after microencapsulation and processes of the food industry as homogeneization and pasteurization and certain types of cooking or house preparates. This implies a novelty in order to add this probiotic organisms to a lot of foodstuffs. Preferably we chose, not limiting, the organisms as follows: probiotic bacteria, optionally acid lactic-bacteria and more preferably chosen among the group: Lactobacillus caseii., L. acidophilus, L. rhamnosus, L. paracasei, L. gasseri, L. fermentum, L. plantarum, L. salivarius, L. crispatus, L. bulgaricus, L. fermentum, L. reuteri, Bifidobacterium infantis, B. bifidum, Streptococcus termophilus, S. bovis, Enterococcus durans, E. faecalis, E. Gallinarum, Escherichia coli, Propionibacterium freudenreicheii, or bacteria or fungi or yeasts genetically modified in that the beneficial genes—characterizing the beneficial properties of probiotic bacteria—have been inserted and also a process of microencapsulation of biologically active materials according to any suitable combination of the preceding claims, characterized in that at least one of the biologically active materials present in the formulation consist in probiotic yeasts, preferably chosen from the group: Saccharomyces cerevisiae, Kluyveromices marxianus, Rhodotorula rubra, Sporobolomyces puniceus, Aureobasidium pullulans, Leucosporidium scotti and also a process of microencapsulation characterized in that at least one of the biologically active materials present in the formulation consist in probiotic fungi, preferably those fungi present in or coincident or coming from cheeses.

The interest in omega 3/6/9 FA has been followed by a huge scientific community, and as well, by Governmentally, University and Medical driven research, proving the benefits of these compounds. Many patents are directed to protection of results that are inferred from such studies (that also include determined ratios of different types of omega FA). This invention is not directed to this patented field, rather to the use of our microcapsules to protect with an extraordinarily better performance in front of state of the art techniques. The inventors, in this regard, investigated the stability and the suitability for microencapsulation of a new type of chemical compounds formed by the esterification of UFAs with sphingolipids, and more precisely with cerebrosides, after consideration of its chemical and biological roles in the development of the brain and specially in the cortex (where the intelligence resides) and other places (e.g. retina). The combination of UFAs with cerebrosides do not have precedent to the best of our knowledge, lesser its use in a covalently bonded compounds (A) and (B), for example, synthesized by the inventor according a modified synthesis according Dondoni et al. (1990), J. Org. Chem. 55(5):1439-1446 and Schmidt and Zimmermann (1986) Tetrahedron 27 (4): 481-484.

We synthesized compound B, R3: CH2CH3, R4: CO—$(CH_2)_2$—$(CH_2$—CH=CH$)_4$—$CH_2$—$CH_3$, with a yield (based on initial arachidonic acid content) of 35%. Due to the small amount of compound synthesized we could only obtain LC-MS data (Agilent 1100 Series LC/MSD Trap) confirming that a peak had the characteristic fractionation peaks of the sphingolipids side together with a typical fragmentation of arachidonic acid (M/Z: 79, 67, 91, 55, 108, 318 [M+]). The analysis of the sphingolipids branch was analyzed also after esterification and benzoylation. Also, we did not observe UV absorption at 205 nm, indicating thus that the double bonds remained without transisomerization. Results were similar when esterifying stearidonate with compound A, in position $R_1$, leading the synthesis to a $R_2$ consisting in H. Therefore, in the present invention we show a microencapsulation method characterized in that at least one of the a.i. (biologically active material) is chosen in between the group of compounds that correspond to the chemical structures (A) and (B), in all their enantiomeric and/or isomeric forms.

Compound(s) A

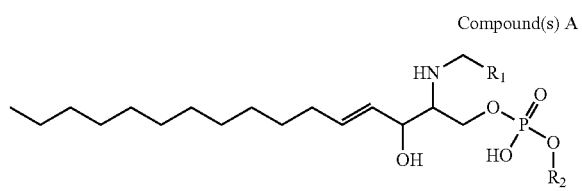

wherein,
$R_1$ is an omega-3 or omega-6 fatty acid ester or omega-9 fatty acid ester
$R_2$ is an omega-3 or omega-6 fatty acid ester Compound(s) B

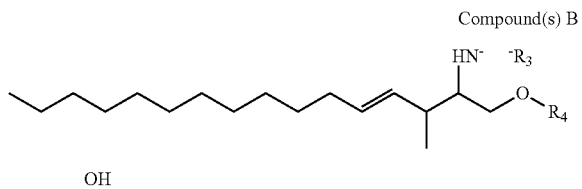

wherein,
$R_3$ is an omega-3 or omega-6 or omega-9 fatty acid ester
$R_4$ is an omega-3 or omega-6 or omega-9 fatty acid ester or an oligosaccharide covalently bound.

This compounds A and B are able to deliver to the body an additional source of cerebrosides and/or sphingolipids not described to the date.

One of the embodiments is a process of microencapsulation characterized in that there exists at least one compound defined by the formulas (A) and/or (B); as well as a formulation of microcapsules to be used for the development of potential intelligence in fetus and breast feeding babies—through the maternal ingestion of a suitable alimentary vehicle in which the formulation of microcapsules is added—and in formulations of milk for babies and children, according the preceding claims, characterized in that contains omega-3 and omega-6 fatty acids in a ratio 0.5-10.0, preferably 1.4-5.7 and contains cerebrosides in a percentage of 0.005%-1% and/or optionally compounds (A) and/or (B), also optionally omega-9 fatty acids; and also a formulation of microcapsules for its use in infant formula according to any suitable combination of preceding claims, characterized in that no omega-6 fatty acid is added and independently and optionally gamma-linolenic acid is added in a percentage of 1.25%.

Concerning the ratios of cerebrosides the formulation of microcapsules used to increase the development of the brain cortex and intelligence, is characterized in that it contains omega-3 and omega-6 fatty acids, preferably in a ratio 1.4-5.7 and contains also cerebrosides in a percentage of 0.005%-1%) and optionally compounds (A) and/or (B).

The fatty acids preferred for this invention refer to the group—also for those substituents of A and B—, not limited to: oleic, steradionic, eicosapentanoic, docosahexanoic, docosapentanoic, linoleic, cojugated linoleic acids, gamma-linolenic, alpha-linolenic, dihomogamma-linolenic, arachidonic and oleic.

These FA may be conjugated with other compounds that provoke their liberation in the human body previous blood transport, being possible to be bonded (maintaining or not all their unsaturations) and/or be covalently bonded with glycerides—mono-, di-, and tri-glycerides preferably), phospholipids, sphingolipids, myelin, amines, ethers, sugars, glycosides, oligosaccharides, nitrogenated and/or oxygenated and/or phosphorated and/or sulfurated heterocycles or substituted aromatic rings.

The arachidonic acid is very unstable by virtue of its high unsaturations (4), as well as other UFAs, and our microcapsules protect the integrity of the original molecules up to its use by the consumer. In the sense of antioxidant protection we propose a formulation consisting in a dispersion of microcapsules characterized in that the active ingredients that are easily oxidable, in particular the unsaturated fatty acids, are protected by means of other active ingredients that can be defined by determined chemical structures or being extracts or juices with antioxidant properties, being the antioxidants, independently from their hydrophobicity in the water phase or in the oil phase, preferably in the phase where the easily oxidable material is present.

A singular aspect of the invention is the ability to release the active content, in a preferred embodiment at pH<3 (thus, releasing the active ingredient only in the stomach). According an experimentally chosen combination of hydrocolloids (taken into account its biodegradability) it can be tailor-made microcapsules with no opening of the microcapsule's wall at pH higher than 3.5, microcapsules that the microcapsules' wall breaking (and subsequent liberation of the content) occurs quickly at pH lower than 3 or characterized in that the breakdown of the microcapsules' wall and the liberation of the content occurs in the conditions of animals' stomach, being the microcapsule's wall materials adequately chosen for the pH range of the stomach of the animal or its ability of enzyme digestion.

FA of long chain (more than 6 carbon atoms), are present in natural sources, w-6 and w-9 being common in plants, but w-3 are more difficult to find in plants, and they are predominant in fishes. Apart from usual (state of the art) sources of w-6 and w-9, other sources of w-3 are:

(a) vegetable origin: Boraginaceae, (*Borago* spp., *Borago officinalis*); Linaceae (*Linum usitatissimum, Linum arvense, Linum sativum*); Onograceae (*Oenothera biennis*); Grossulariaceae (*Ribes nigrum*), *Zea Mais, Gossypium hirsutum, Carthamus tinctorius, Glycine max.*

(b) algae preferably: Graciliariceae (*Gracilaria* spp); Gigartinaceae (*Iridaea* spp.); Kallymeniaceae (*Callopyllis variegata*); Durvillaceae (*Durvillaea antartica*); Solieriaceae (*Euchema cottoni*); Gelidiaceae (*Gelidium* spp); Lossoniaceae (*Lesonia nigrescens*); Gigantinaceae (*Gigartina* spp.); Lessoniaceae (*Macrocystis* spp.); Bangiaceae (*Porphyra* spp.); *Crypthecodinium* spp.

(c) Animal origin, normally fish oil, preferably: Engaulidae (*Lycengraulis olidus*); Clupeidae (*Sardina pilchardus*); Scomberesocidae (*Scomberesox saurus scombroides*); Berycidae (*Beryx splendens*); Engraulidae (*Engraulis ringens*); Ophichthyidae (*Ophichthus* spp.); Serranidae (*Hemilutjanus macrophthalmus*); Scombridae (*Thunnus* spp., en especial, *Thunnus albacares, Thunnus alalunga, Thunnus obesus*); Sciaenidae (*Cynoscion analis*); Carcharhimidae (*Prionace glauca*); Normanichthyidae (*Normanichthys crockeri*); Percichthyidae (*Polyprion oxygeneios*); Notothenidae (*Dissostichus eleginoides*); Apogonidae (*Epigonus crassicaudus*); Branchiostegidae (*Prolatilus jugularis*); Scombridae (*Thunnus* spp., *Thunnus albacares, Thunnus alalunga, Thunnus obesus, Sarda* spp., *Sarda chiliensis, Scomber japonicus peruanus*), Sciaenidae (*Cynoscion analis*), Carcharhimidae, Normanichthyidae (*Normanichthys crockeri*); Percichthyidae (*Polyprion oxygeneios*); Notothenidae (*Bacalao de profundidad*); Apogonidae (*Epigonus crassicaudus*); Branchiostegidae (*Prolatilus jugularis*); Cheilodactylidae (*Cheilodactylus gayi*); Gadidae (*Salilota australis*); Pomadasyidae; Scorpaenidae; Serranidae; Cyprimidae; Monacanthidae; Centrolophidae; Ophidiidae; Scorpaenidae; Coryphaenidae; Channichthydae; Sciaenidae; Aplodactylidae; Carangidae (*Trachurus symetricus murphyi*); Bothidae (*Paralichthys microps*); Mugilidae; Clupeidae; Priacathidae; Merlucciidae (*Merluccius gayi gayi, Merluccius australis*); Macruronidae (*Macruronus magellanicus*); Gadidae (*Micromesistius australis*); Girellidae; Trachichthyidae; Carangidae; Kyphosidae; Callorhynchidae; Labridae; Macrouridae; Atherimidae; Gobiesocidae; Alopiidae; Galaxiidae; Rajidae; Bramidae; Carangidae; Notothenidae; Scianidae; Mugiloididae; Salmonidae (*Salmo* spp., *Salmo salar, Oncorhynchus* spp., *Oncorhynchus kisutch, Oncorhynchus mykiss, Oncorhynchus tshawytscha*); Clupeidae (*Sardinops* spp., *Sardinops sagax, Clupea bentincki*); Pomadasyidae; Gempylidae; Lamidae (*Isurus* spp., *Isurus oxyrinchus*); Triakidae; Climidae; Scophthalmidae; Labridae; and more preferably Atlantic mackerel, *Engraulis encrasicholus, Pomatomus saltatrix, Sarda sarda, Sardina pilchardus, Brevoortia tyrannus, Brevoortia patronus, Chloroscombrus chrysurus, Auxis thazard, Scomber scombrus, Scomber japonicus, Alosa aestivalis, Clupea harengus, Etrumeus teres, Argentina silus, Ictalurus punctatus.*

(d) microbial origin, preferably: *Saccharomyces cerevisiae, Escherichia coli, Schizochytrium* spp., *Thraustochytrium aureum, Thraustochytrium roseum, Thraustochytrium striatum, Mortiriella* spp., *Phytium* spp., *Aspergillus* spp. *Aspergillus nidulans, Aspergillus sydowi, Fusarium* spp., *Fusarium equiseti, Fusarium oxysporum.*

One of the embodiments of the invention is a microencapsulated formulation for increasing the neural development, specially the brain and more specially in unborn, newborn, babies and kids characterized in that at least it is present one of the compounds with the formula B and/or A.

Other embodiment is the use of a microencapsulated formulation for increasing the potential intelligence in unborn and babies feed with mother milk, by means of the consum on the side of the milk-giving woman in an appropriate foodstuff where it is added the microencapsulated formulation. Also for infant food and milks, characterized in that it contains w-3 and w-6 in a ratio of 0.5-10 preferably 1.4-5.7, and moreover it contains cerebrosides in a percentage of 0.005% and 1% and/or optionally compounds A+B. There are many recommended ratios of w-3 to w-6, without a firm scientific base. On the other side there exist patents that cover all imaginable combinations of ratios. The inventors adopt a range more accepted by medical institutions from different countries. The novelty of the present invention is the incorporation of cerebrosides and optional compounds A+B, as well a way to provide to the consumer UFAs without the presence of bad or off-aromas or degradation products of the UFAs. The inventors have verified that in an industrial process to prepare milk with w-3, the 50% of the initial content in w-3 is lost during homogenization and pasteurization. Our microcapsules, industrially, in the worst case, proven in a pilot plant, we obtain a maximum in losses of w-3 of 7%. We claim as well a formulation of microcapsules for its use in infant formula characterized in that no omega-6 fatty acid is added and independently and optionally gamma-linolenic acid is added in a percentage of 1.25%. Also, in a preferred embodiment we use a microencapsulated formulation for increasing the development of the brain cortex and the intelligence, characterized in that contains omega-3 and omega-6 fatty acids in a ratio 0.5-10.0, preferably 1.4-5.7 and contains cerebrosides in a percentage of 0.005%-1% and/or optionally compounds (A) and/or (B).

The inventors have formulated a beverage (soft drink) Beverage containing a formulation of microcapsules, characterized in that the beverage contains microcapsules, and the latter contain in the oil phase omega-6 and/or omega-3 fatty acids, optionally with antioxidants added in the aqueous phases of the microcapsule or in the oil phase of the microcapsule or in both and the beverage contains additionally flavours or extracts of: grape, pineapple, and at least a citric fruit, preferably selected from tangerine, orange, mandarin, lemon, lime, and the omega-3 and omega-6 fatty acids remain stable in the beverage after the industrial process, including customary microbiological stabilization processes like pasteurization, at least up to one month, with a loss of omega-3 less than 7%. After more than one hundred trials to try to mask the off-flavor of omega-3 sources, the inventors tried the best solution with a tasting panel that was not able to detect the presence of the aroma of fish oil or flax oil. Another embodiment of the invention is a juice containing microcapsules of our invention characterized in that (a) the microcapsules contain omega-3 fatty acids coming from a commercial formulation of edible linseed oil; (b) the oil phase contains the linseed oil and an emulsifier based on soja compounds; (c) the water phase contains a mix of different subclasses of hydrocolloids of the type alginates and/or Arabic gum and/or kappa-carrageenate and/or guar gum, also an edible primary emulsifier with HLB in between 10 and 14 and an edible viscosity modifier; (d) the pH of the formulation of microcapsules is 3 to 6, the particle size median of the freshly produced microcapsules is 1-10 μm; (e) the main ingredient of the juice is orange juice. Optionally the fruits that constitute the juice are chosen from the group: critics, pineapple, grape and in that contain (all data referred to 150 mL of juice) w-3 in the range 20-200 mg, w-6 in the range 10-100 mg and w-9 in the range of 5-50 mg; with a ration w-3:w-6 of about 3:1.

Playing with the hydrocolloid or hydrogel type, the inventors are able to formulate microcapsules that are destroyed at low pH (like that present in the human stomach) or are resistant to low pHs (and can pass through the stomach—convenient for certain hormones like insulin—and the wall microcapsule being broken when the pH in the intestine is increased), as well as walls that can be attacked by bacteria (e.g., using starch as a wall materials, the amylases would destroy the wall), or by pressure by chewing, or to be gelified in the presence of saliva, releasing a flavour (e.g., menthol) in a very fast way. Since in no way the invention is limited for human consume, the microcapsules may be designed for the conditions particular to each animal (e.g., the pig has many amylases in the mouth to the difference of the men, and a microcapsule formulated with starch as wall material would be appropriated to give to the food a better taste to increase the food ingestion, therefore, the benefit os the farmer).

The microcapsules and appropriate formulations are compatible and desirable for foods in which the active ingredients come from agriculture (term including fisheries and animals' farming) "biological" and/or ecological", because this falls in the line with a healthy diet without intervention of products strange to the nature. Obviously, in this embodiment, and in many others, all the materials must be edible.

In another embodiment, with an spirit completely contrary to the one said in the beforementioned paragraph, the formulation uses for the obtention of the active ingredients, GMOs, hybrid vegetal varieties or obtained be human selection, as well as microbiological cultures selected by any technique. This embodiment is possible but not desired because the consumers generally avoid GMOs.

Apart from alimentary uses, the microcapsules produced by our processes can be included in medicinal formulations, combined with active compounds not present in the microcapsules or being the active ingredients present in the microcapsules (or formulation of microcapsules) the only active ingredients of the medicinal preparation, including under the term medicinal preparation also materials for its use in radiology contrasts, seed for oncological radiotherapy, thermotherapy or therapy by irradiation with light of any wavelength. In a preferred embodiment, radiological contrasts are very appropriate to be combined (used as a.i.) with our microcapsules that allow the transit through the stomach without being degraded and finally excreted, for medical uses (e.g., detection of bleedings by virtue of the degradation of microcapsules' wall materials sensitive to enzymes of the blood plasma).

Because many of the healthy active ingredients are labile, specially to oxidation, an embodiment is to keep separated the capsules separated from the food or beverage until the final consumption of the product, optionally with a receptacle that by pressure liberates the microcapsules' formulation, preferably dried, to the food or beverage.

For a better understanding of the invention, 19 figures are enclosed, which explanation is better understood when reading the example to which they refer.

BRIEF DESCRIPTION OF THE SEVERAL VIEWS OF THE DRAWINGS

In FIG. 7 we show the final structure of a microcapsule that due to the process of breaking and reconstitution showed in FIG. 6, may exists small microcapsules (25, 21) inside bigger microcapsules (22), showing also the protective colloid 18 and the polymerized and crosslinked hydrocolloid(s) 19. In 7b we have a microcapsule where an additional hydrocolloid (dotted line 40) has being incorporated (e.g., chitosans) the reinforce the microcapsules.

EXAMPLES

Figure 1:
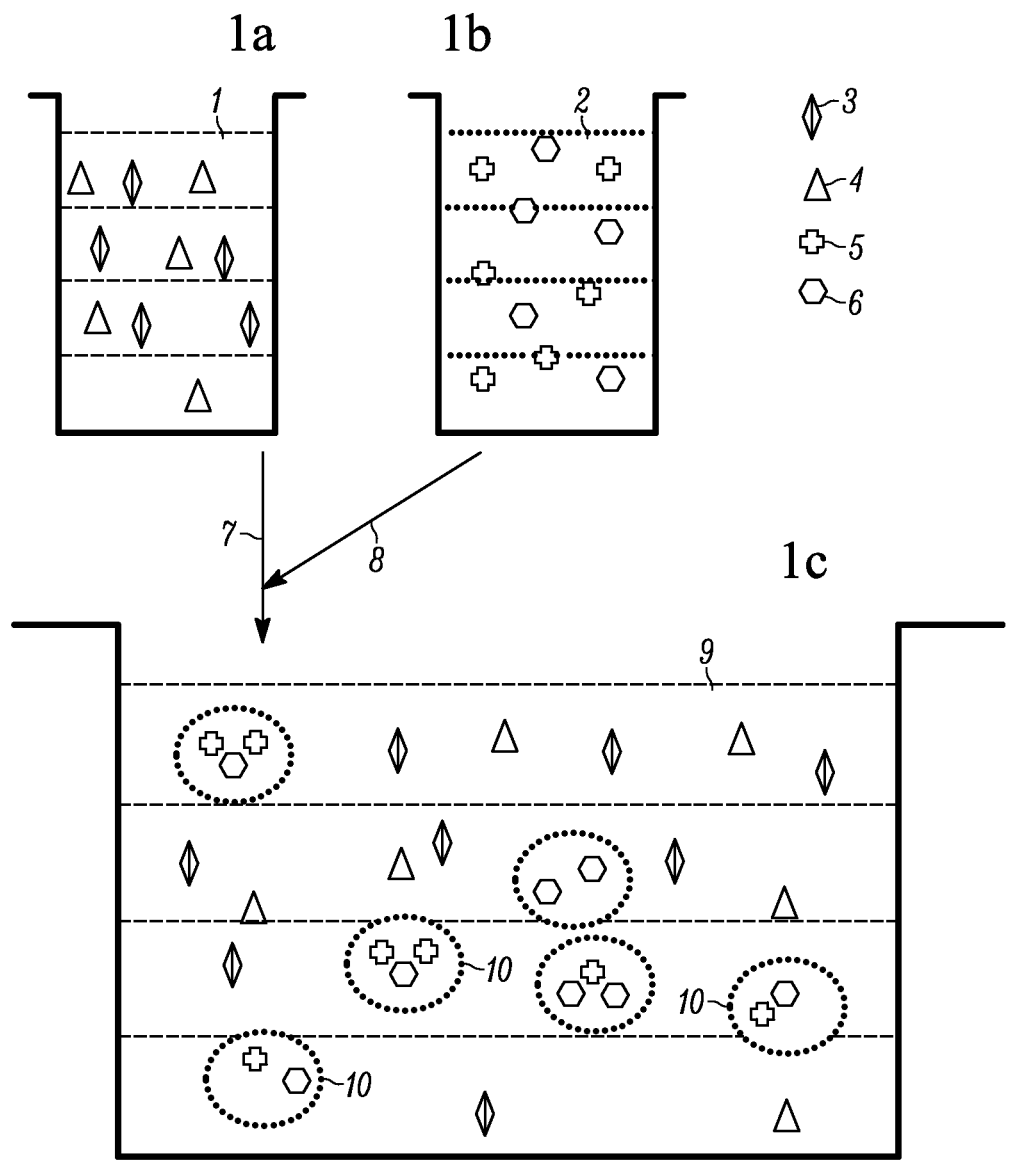
FIG. 1 shows the first emulsion to be formed with different biologically active ingredients (3, 4, 5, 6), being 1a the oil phase (oil: 1) and 1b the water phase (2: water). 1b is added to 1a as arrows 7 and 8 show, forming the emulsion 1c, with water droplets 10 in the oil phase 9.
Figure 2:
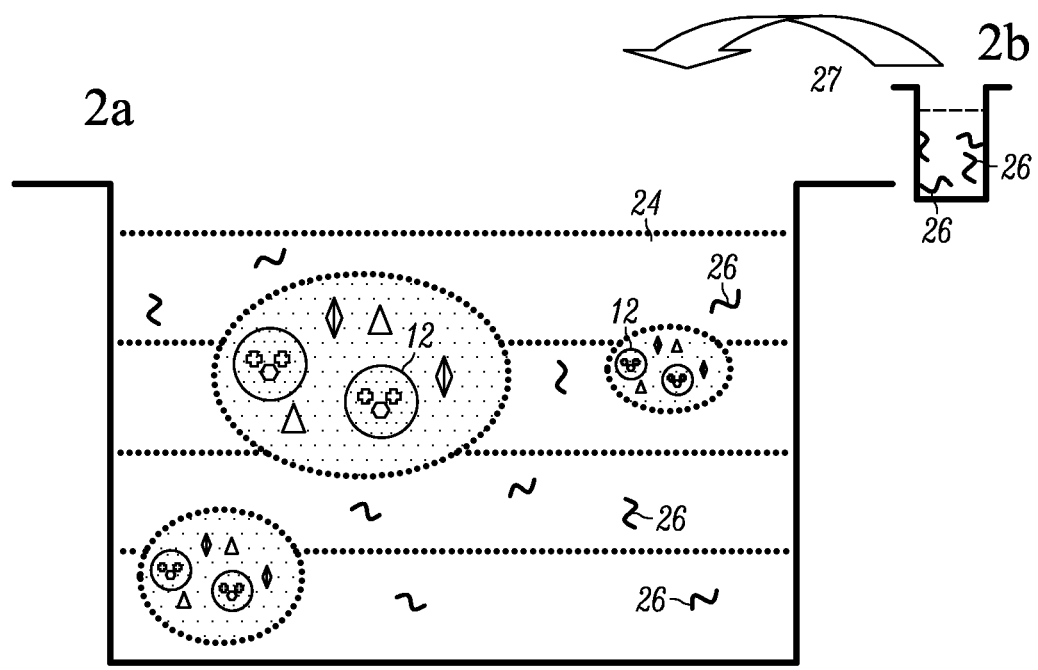
FIG. 2 shows the addition (arrow 27) during the process of the hydrocolloid (26) solution 2b, to the former emulsion solution 1c, now represented after such addition by 2a. We can find in 2a the W/O/W emulsion-dispersion, the water continuous phase being 24, 11 representing the water in oil dispersed emulsion that will represent the core of the microcapsules, and 12 the inner water phase of the "oil" droplets 11.
Figure 3:
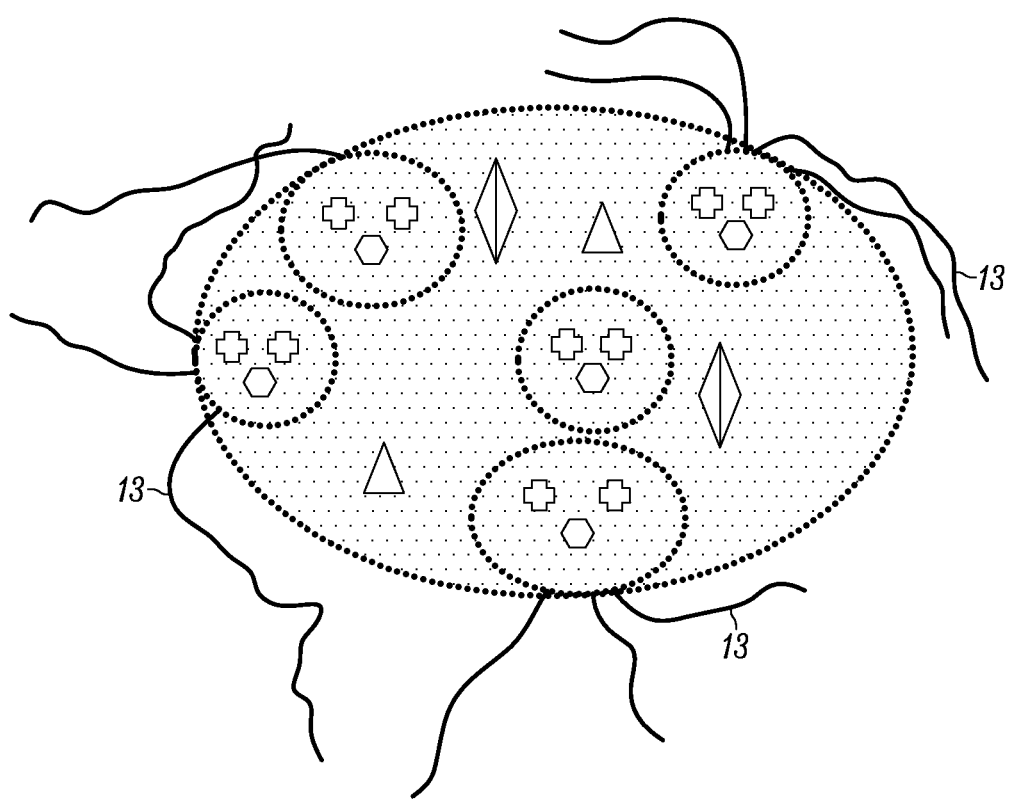
FIG. 3 represents the polymerization reaction of the hydrocollois(s) taking place in the water phase.
Figure 4:
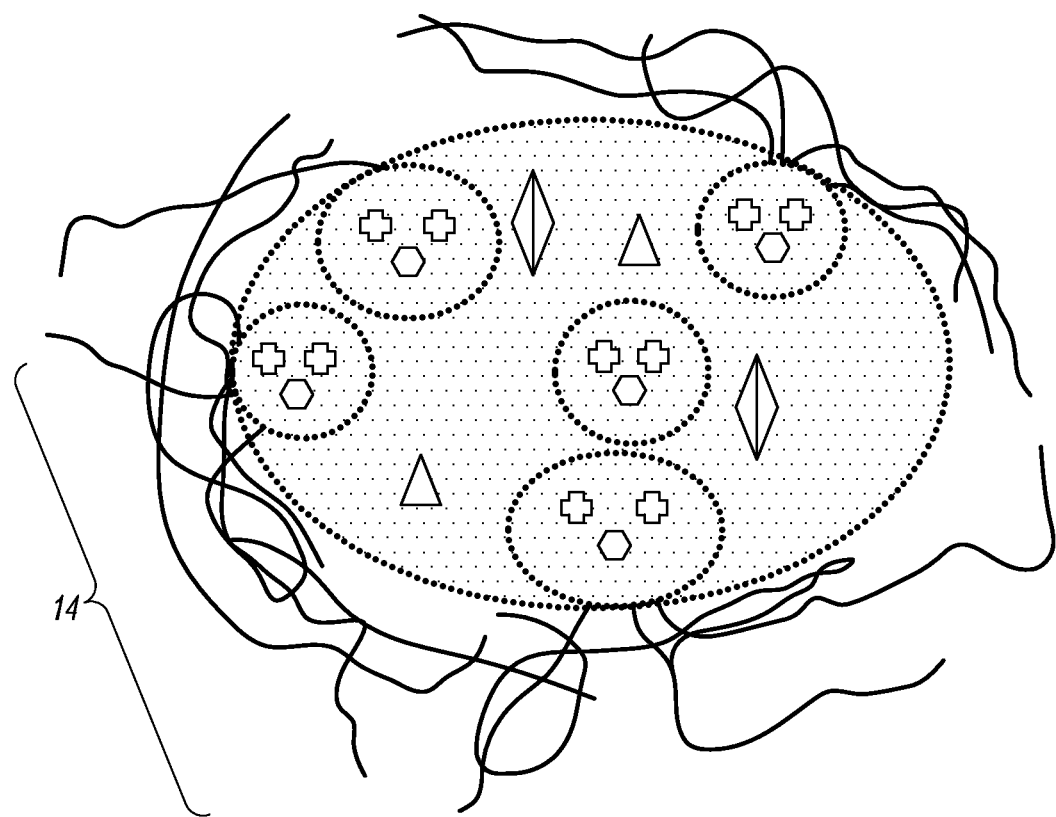
FIG. 4 is a more advanced status of polymerization where the hydrocolloids (14), apart from being polymerized are being cross-linked.
Figure 5:
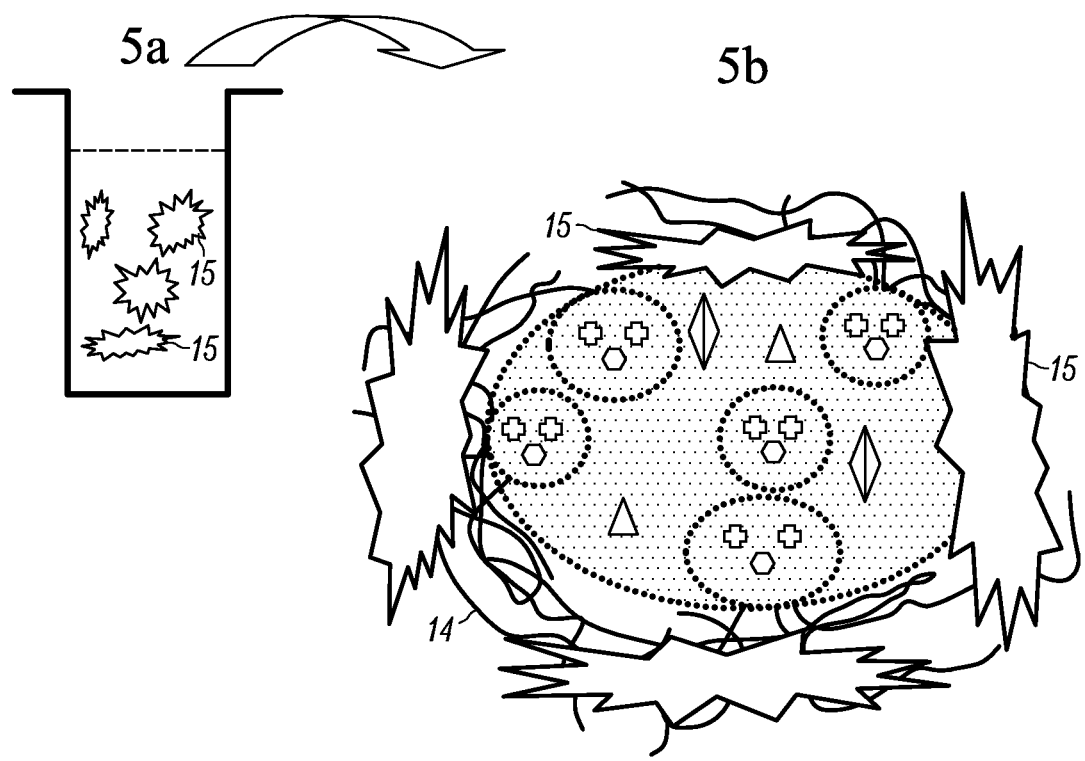
FIG. 5 shows the addition of the protective colloid(s) 15, that will be integrated in the polymeric structure 14, being 5a the protective colloid(s) solution and 5b the representation of the incorporation of the protective colloid to the incipient microcapsules.
Figure 6:
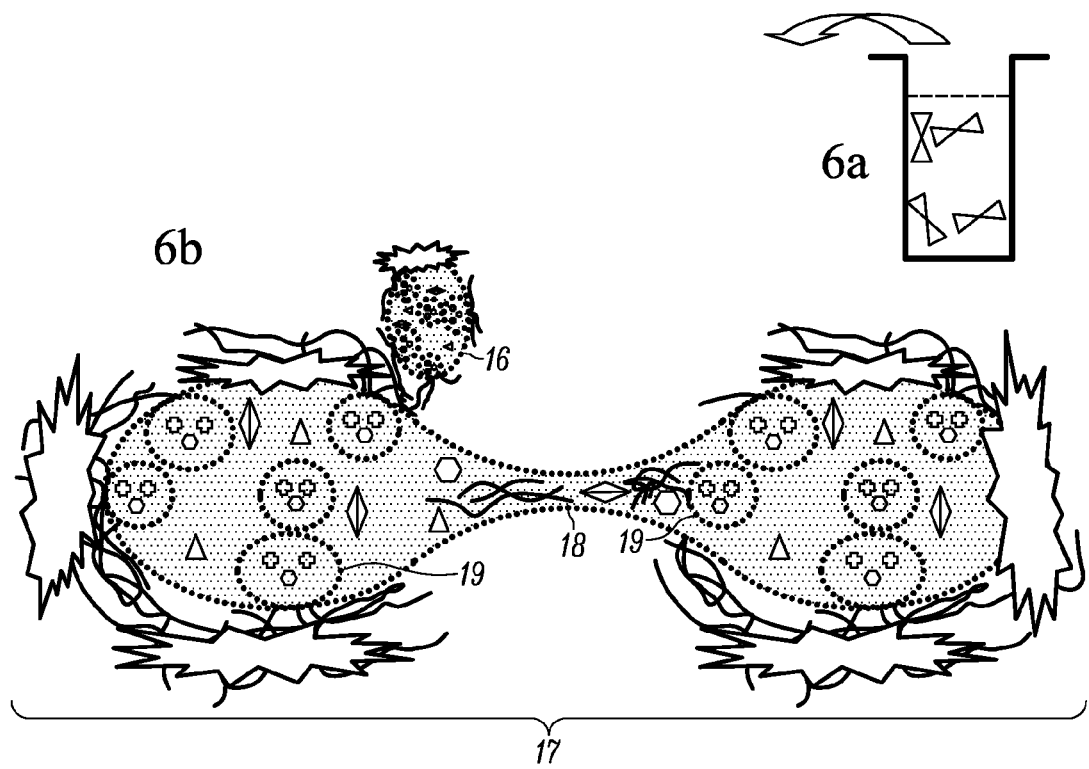
FIG. 6 shows the solution of primary emulsifier 6a that is added to the continuous water phase (24) represented in FIG. 2, 2a. 17 shows that this primary emulsifier (that may be composed of different types of state of the art emulsifiers for emulsions oil in water or mixtures of such emulsifiers with those used for oil in water emulsions) allows the breakdown on the half-formed microcapsules, allowing the reduction of the particle size.
Figure 8:
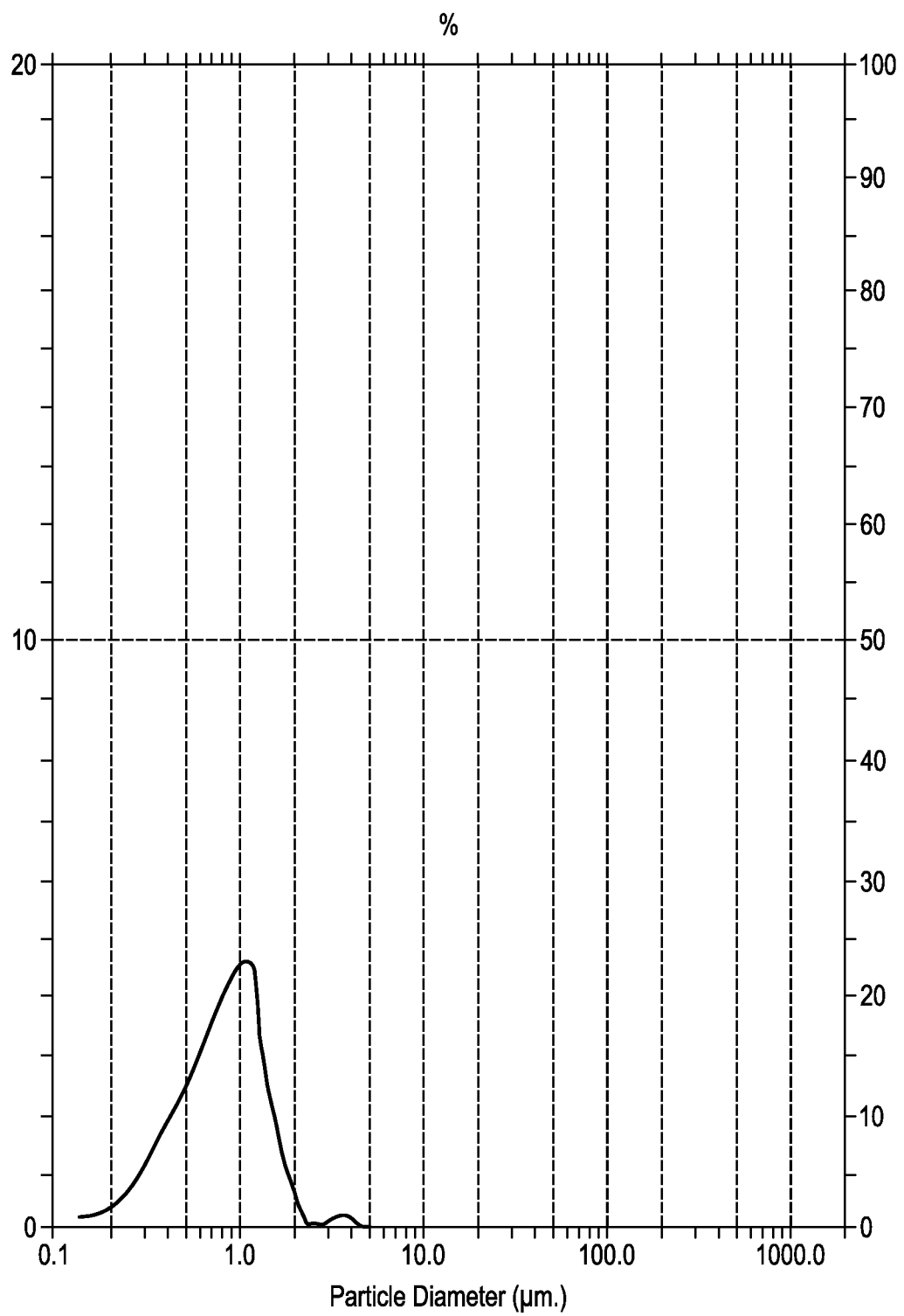
FIGS. 8 and 9 show typical particle size distribution of our microcapsules.

The following examples are given for illustrative purposes and they cannot be considered as a restriction to the claimed formulation, in so far, changes from the here presented examples are overcome easily in laboratory formulations and/or in bulk production.

Also, the applicant has developed proprietary methods to analyze formulations made by means of the herein disclosed procedures, in order to determine unambiguously, when a formulation has been done with the information provided in the present document. These methods of analysis are also available in order to comply with Health and Governmental regulations for approval of new-marketed products.

Example 1

In this example we describe the active ingredients used to make a formulation suitable for its application to orange juice.

1.1.—Ingredients

|  | [%] |
|---|---|
| Oil Phase | |
| Flaxoil | 25.00 |
| Emulpur | 1.00 |
| Water Phase | |
| Dest. Water* | 20.00 |
| Rosemary extract | 2.80 |
| Juice from carrots | 7.30 |
| Orlistat (lipase inhibitor) | 1.00 |

1.2.—Encapsulation and Emulsification Ingredients

|  | [%] |
|---|---|
| Alginate solution** | 25.00 |
| Guar gum (4% in water) | 15.40 |
| Lamegin | 2.50 |
| Keltrol | 0.30 |

* plus 0.5% $CaCl_2$, 0.1% ascorbic acid, 0.08% nipagil [all in water].
**Alginate solution = 5% Manucol LB in water 1.2 Process:

| oil phase: | weigh in a bottle, homogenize in an ultrasonic bath |
|---|---|
| water phase | weigh in a bottle, homogenize in an ultrasonic bath |
| W/O emulsion | put the oil then the water phase in the reactor, make the emulsion with stirrer at 7350 rpm, 25 min |
| (W/O/W) emulsion | add the alginate solution, stirrer at 350 rpm at 35° C. |
| Decrease of particle | shortly after add the Arabic gum, stir at 8350 rpm at 35° C. |
| Further decrease of particle size | shortly afterwards, add the Lamegin, Ultraturrax 8135 rpm at 35° C. |
| Curing of the microcapsules | 3000 rpm for 120 min at 75° C. |
| Addition of viscosity modifier | after 20 min add Keltrol, at 5000 rpm |
| Cooling down | stop water bath, cooling down to 5-10° C. |
| Fill up | fill up directly in package. |

Physiochemical Parameters:

| pH = 6.5 | |
|---|---|
| Particle size: | |
| D (v; 0.5): 12.57 μm [median] | D (v; 0.9): 26.39 μm [percentile 90] |

Examples 2-11

In Table 1, we present a series of microencapsulation processes. These microencapsulations have been made following the general procedure described above. With the data provided in previous patents are in many cases not enough to reproduce or to get the claimed formulations.

Both components and results of the tests are shown in table 1.

Formulation components active ingredients are described, those of the oil phase and also those of the water phase. The data provided about particle size correspond to the percentile 50—D (v; 0.5)—and percentile 90—D (v; 0.9)—.

We can see in the last row the quality of the resulting formulation. As we can see, small changes in composition may lead to a bad formulated microencapsulated material.

Example 12

In the present embodiment, we show the release of microcapsules at a certain pH. Microcapsules break down at stomach pH, while the microcapsules stay intact in the yogurt, which is also acidic (but not as highly acidic as the stomach).

The objective of the present example is to test the release rate of microencapsulated riboflavin (according to the present invention) present in a probiotic yogurt.

The yogurt has been prepared (20 kg) in a traditional, hand-made, way, using an "in-house" culture of fermentation kept from the last yogurt production.

The composition of the formulation (percentage with respect to total active ingredients) is:

Riboflavine 100 μg/kg yogurt (less than 0.1% of the total active ingredients)

*Lactobacillus casei* 10% (solution in water of a culture with 500 colonies per $cm^2$)

*Avena sativa* extract 90%

The formulation has been prepared following the general procedure of encapsulation, with alginates as the cross-linked hydrocolloid and a mixture of Ceratonia siliqua gum and arbabic gum as protective hydrocolloids.

A non-encapsulated material has been included in the experiment to show the differences, and also a blank sample.

A) Test in acidic media (1 HCl, buffer at pH 2.5)—conditions in the stomach

B) Test the delivery rate of vitamin B2, in an isotonic solution at pH 4.0—conditions in an organic yogurt—produced in an organic farm—.

A—Results in Acidic Media—

It is clearly shown, that release of Vitamin $B_2$ from the Formulation GAT 032541 occurs in stomach conditions.

The average amount of released Riboflavin happens after 30 min. is 21.5 μg/kg [it is said, a conversion of the weighted sample of ca. 30-40%]; after 60 min., are released 25.7 μg/kg [it is said, a conversion of the weighted sample of ca. 40-50%].

The release rate in non-encapsulated material is, as expected, higher. After 30 min., the average released amount of Vitamin $B_2$ is 46.8% [it is said, 40-50% of the weighted sample]; after 60 min., are released 47.2 μg/kg [it is said, a conversion of the weighted sample of ca. 65-75%].

The blank did not show any release (gas-liquid chromatographic peak) of Riboflavin.

B—Results in Yogurt Media—

Formulation GAT 032541 does not release any vitamin $B_2$, while being in the yogurt, at least for one and a half month.

The non-encapsulated sample showed a slight release of 0.021 μg/g after 30 min., and 0.032 μg/g after 60 min.

The blank samples did not show any noticeable change in Vitamin B$_2$ content.

Example 13

One of the innovative aspects of the present invention is its ability to keep the active ingredients stable for longer time with respect to the state in the art microencapsulation and even any other method of formulation. This obviously does not apply for stable active ingredients (e.g. minerals).

We have performed tests of storage ability while remaining the active ingredients unchanged.

The process of encapsulation is basically as the one presented in the example 1, with the exception that the secondary wall is formed with xanthan gum (from Fluka), the emulsifier is Softenol® 3767 (1%) and the viscosity modifier is Glycosperse® (1%), the source of w-3 and w-6 fatty acids was fish oil (*Clupea harengus*).

Results of this experiment are showed in the following table, where we appreciate that the stability of the fatty acids, for 60 days at 45° C. is exceptional.

|  | Palmitic acid % in the oil | Stearic acid % in the oil | oleic acid % in the oil | linoleic acid % in the oil | alpha-linolenic acid % in the oil | w-3 acids % in the oil |
|---|---|---|---|---|---|---|
| d = 0 | 1.1 | 1.4 | 2.9 | 2.8 | 2.7 | 7.8 |
| d = 30; 4° C. | 1.1 | 1.4 | 2.7 | 2.6 | 2.5 | 7.8 |
| d = 30; 25° C. | 1.1 | 1.4 | 2.6 | 2.6 | 2.6 | 7.7 |
| d = 30; 45° C. | 1.1 | 1.3 | 2.6 | 2.5 | 2.5 | 7.7 |
| d = 60; 45° C. | 1.1 | 1.3 | 2.4 | 2.5 | 2.4 | 7.5 |

Example 14

The major problem associated with developing new formulations is the difficulty to infer the actual results from past formulations. As far as many components (and quantities) may be present in a microencapsulation, the number of experiments needed for a good statistical validation is enormously high. We have overcome this problem with the state in the art statistical techniques associated to experimental design. We have used a Folded Plackett-Burman experimental design (we are interested only in the main factors, and not in interactions for the purpose of this analysis), with 3 center points and an acceptable level of error degrees of freedom (19). This accounts for 27 runs (instead of the 64 needed in a regular experimental design—all combinations—) in order to investigate the influence in the final formulation of:

Oil phase (grape seed oil [50%]+salmon fish oil [50%]): 2 levels, 10%-30%

Natural extract (grape marks [50%]+green tea decaffeinated [50%]): 2 levels, 10%-20%

Alginate solution: 2 levels, 5%-10%

Carrageen gum solution: 2 levels, 5%-10%

Yucca glauca extract: 2 levels, 3%-5% homogenization: 2 levels, present-not present

Spray drying: 2 levels, present-not present The independent variable is in this case, a value that reflects the suitability of the microencapsulation for industrial purposes, in particular, to add to soft drinks. To evaluate this "acceptability index" we have used the expression:

$$AccIndex = \frac{\left(\begin{array}{c} 0.20*ParticleSize + 0.30*Density + 0.15* \\ UnreactedPolymers + +0.15* \\ DegreeMultiencapsulation + 0.20* \\ UnencapsulatedIngredients \end{array}\right)}{1} * 100$$

We have developed, through a series of experiments a table that gives, for each Particle Size (and the other variables) a value in between 0 and 1. "Density" (not the actual meaning of density) may have value 0, because outside a defined range, the density is not considered; also, the acceptability index depends of the constraints of the other variables (e.g., if the degree of unreacted polymers is higher than 40%, we give to the acceptability index a value of 0, no matter the value of the rest of the parameters). The constant values that account for the weight of each value have been developed specially for soft drinks. It is clear that behind these experimental design there is much work involved.

This way, we obtain (Statgraphics®) a randomized design as follows, being "−1" the lower level and "1" the higher level (last column, Acceptability Index):

| run/test | Oil | Plant | Algin. | Xanth. | *Yucca* | Hom. | Spray | Acc. Index |
|---|---|---|---|---|---|---|---|---|
| 1 | 0.0 | 0.0 | 0.0 | 0.0 | 0.0 | 0.0 | 0.0 | 0 |
| 2 | 1.0 | −1.0 | −1.0 | −1.0 | 1.0 | −1.0 | −1.0 | 10 |
| 3 | 1.0 | −1.0 | 1.0 | 1.0 | −1.0 | 1.0 | −1.0 | 95 |
| 4 | 1.0 | 1.0 | −1.0 | 1.0 | 1.0 | −1.0 | 1.0 | 60 |
| 5 | 1.0 | 1.0 | −1.0 | −1.0 | −1.0 | 1.0 | −1.0 | 84 |
| 6 | −1.0 | −1.0 | 1.0 | −1.0 | 1.0 | 1.0 | 1.0 | 32 |
| 7 | 1.0 | −1.0 | 1.0 | −1.0 | −1.0 | −1.0 | 1.0 | 20 |
| 8 | 0.0 | 0.0 | 0.0 | 0.0 | 0.0 | 0.0 | 0.0 | 0 |
| 9 | −1.0 | 1.0 | 1.0 | 1.0 | −1.0 | −1.0 | −1.0 | 60 |
| 10 | −1.0 | −1.0 | −1.0 | 1.0 | −1.0 | −1.0 | 1.0 | 30 |
| 11 | −1.0 | 1.0 | 1.0 | 1.0 | 1.0 | −1.0 | 1.0 | 28 |
| 12 | 1.0 | 1.0 | −1.0 | 1.0 | −1.0 | 1.0 | −1.0 | 45 |
| 13 | 1.0 | −1.0 | 1.0 | 1.0 | 1.0 | −1.0 | −1.0 | 31 |
| 14 | −1.0 | 1.0 | 1.0 | 1.0 | −1.0 | 1.0 | 1.0 | 69 |
| 15 | −1.0 | −1.0 | 1.0 | 1.0 | 1.0 | 1.0 | −1.0 | 85 |
| 16 | 1.0 | −1.0 | −1.0 | −1.0 | 1.0 | 1.0 | 1.0 | 93 |
| 17 | −1.0 | 1.0 | −1.0 | −1.0 | −1.0 | 1.0 | 1.0 | 15 |
| 18 | −1.0 | −1.0 | −1.0 | −1.0 | −1.0 | −1.0 | −1.0 | 7 |
| 19 | 1.0 | −1.0 | −1.0 | 1.0 | 1.0 | 1.0 | 1.0 | 54 |
| 20 | −1.0 | 1.0 | −1.0 | 1.0 | 1.0 | 1.0 | −1.0 | 61 |
| 21 | −1.0 | −1.0 | 1.0 | −1.0 | −1.0 | 1.0 | −1.0 | 12 |
| 22 | 1.0 | 1.0 | 1.0 | 1.0 | 1.0 | 1.0 | 1.0 | 69 |
| 23 | 1.0 | 1.0 | 1.0 | −1.0 | 1.0 | −1.0 | −1.0 | 81 |
| 24 | 0.0 | 0.0 | 0.0 | 0.0 | 0.0 | 0.0 | 0.0 | 0 |
| 25 | −1.0 | 1.0 | 1.0 | −1.0 | 1.0 | −1.0 | −1.0 | 20 |
| 26 | 1.0 | 1.0 | 1.0 | −1.0 | −1.0 | −1.0 | 1.0 | 17 |
| 27 | −1.0 | 1.0 | −1.0 | 1.0 | −1.0 | 1.0 | 1.0 | 72 |

The results of the ANOVA analysis showed in Table 2 show that all the parameters studied influence the final product acceptability. This is indicated by the p-value (<0.05 in all cases), as any skilled in statistics would appreciate. Thus, in developing a formulation of health improving soft drinks, we cannot neglect any of the effects of all the variables tested.

It is remarkable that most important parameter in this type of microencapsulation for soft drinks, the homogenization has extreme influence in the final microcapsules.

Example 14

We have tested the stability of a formulation (according to example 9, improving the previous results with addition of a secondary emulsifier—span 65, 5%—) of spores of *Bacillus subtilis*. Later we tested that actually the spores were viable (seeding in potato dextrose-agar with development of colonies).

Figure 9:
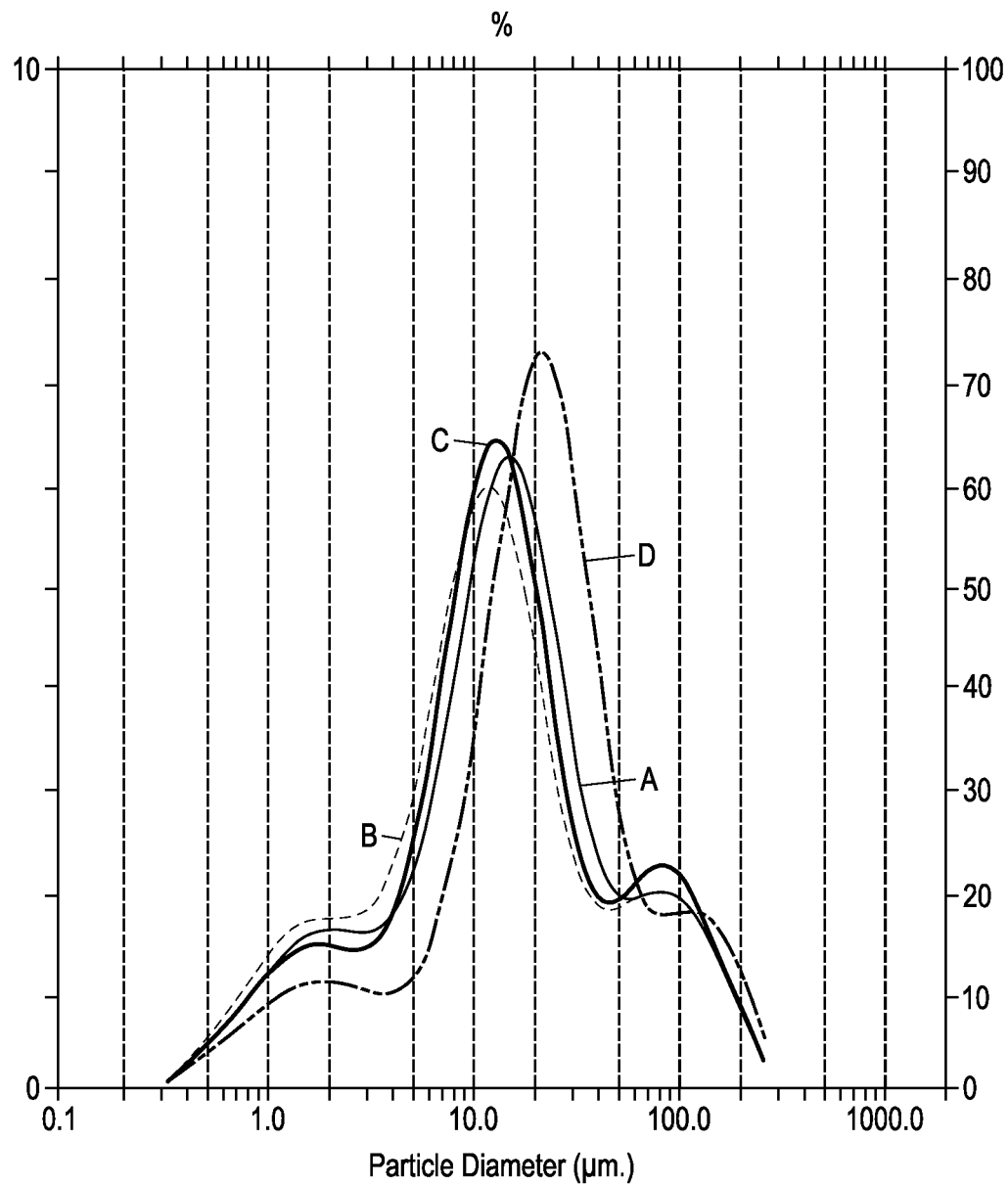

Results of the stability of the microcapsules, based on the stability of the particle size of the dispersion, at different aging times, are shown in FIG. 9. There it is show the distribution of the particle size of the microcapsules (the outer diameter, when in the case of multiencapsulation). The different curves obey to different storage times and temperatures.

A=initial (time=0, T=25° C.)
B=after 60 days at 3° C.
C=after 60 days at 25° C.
D=after 90 days at 25° C.

The shape of the curves is homogeneous, meaning that the breakdown of the capsules has not occurred.

Note that the particle size is that of the microcapsules (values are plotted when the counter has arrived to 1,000,000 particle size measurements). If we had spores released into the media, the shape of the curve would have changed, and also shifted to the left, because the spores of *Bacillus subtilis* are in the range 1 to 2 µm.

Example 16

In the method of analysis of formulations, we have obtained the diagrams of viscosity vs. shear stress.

Figure 10:
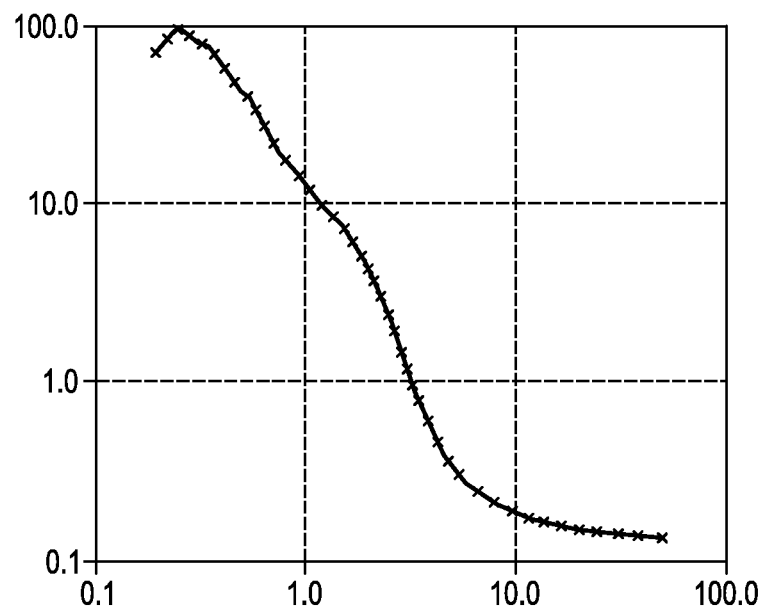
FIGS. 10 to 13 show typical tau vs. nu viscosigrams of our formulated microcapsules.
Figure 11:
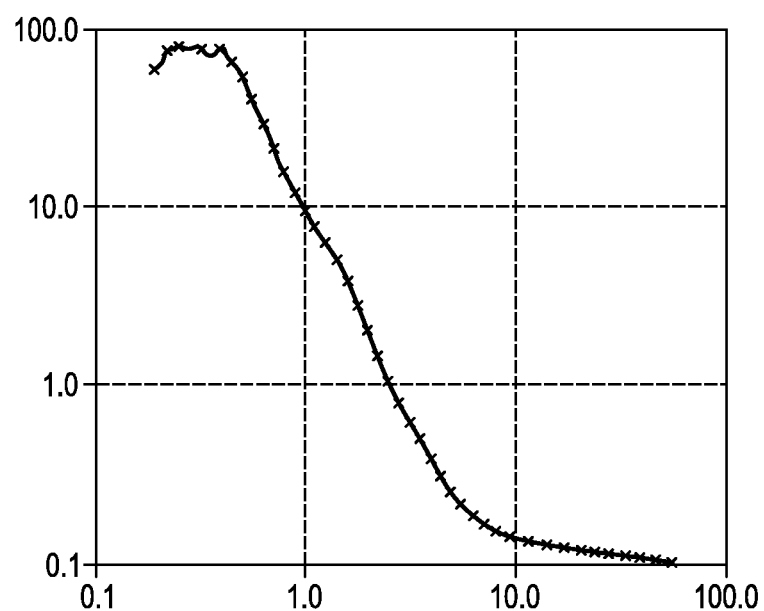
Figure 12:
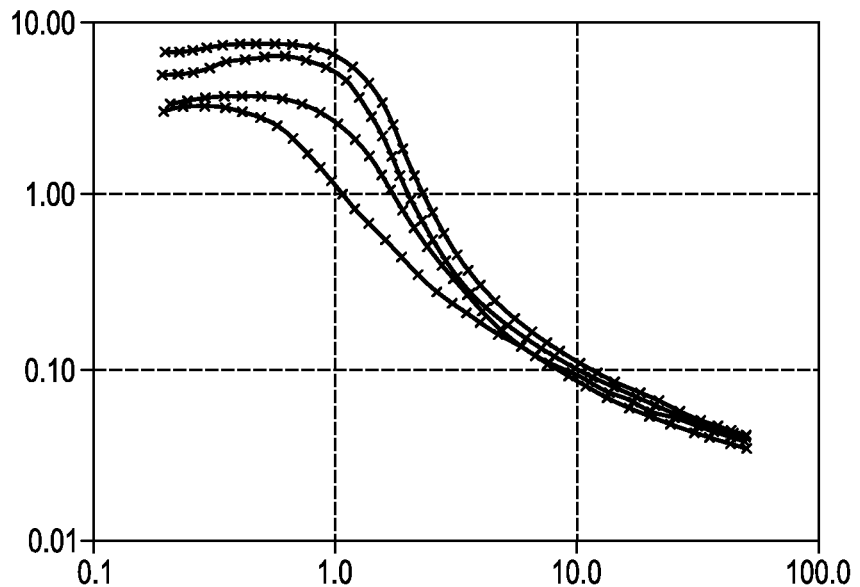
Figure 13:
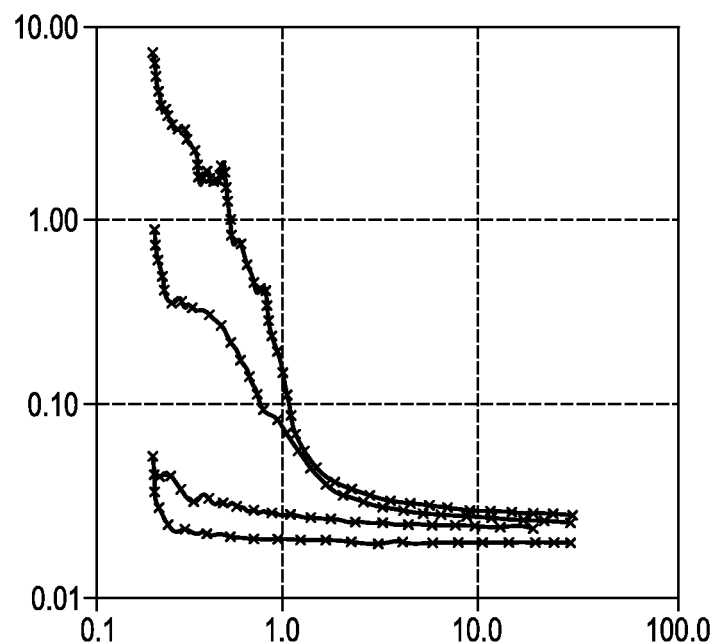

The peak showed in FIGS. 10 to 12 is characteristic of our formulation. It indicates that the microencapsulated formulation diminishes progressively its internal structure due to the force applied (shear stress), but after a period of time (force) while the cohesive forces that keep the macromolecular structure of the formulation stable are broken (namely, until the peak shown). Note that the microcapsules are not broken, rather, the structure that keeps the microcapsules in dispersed, without precipitation, coacervation or any distortion of the formulation. When the macromolecular cohesive forces (mainly electrostatic forces) are low (FIG. 13) we do not observe any peak, but a progressive decrease in the viscosity with shear stress applied, because, in such lower viscosity range, the cohesive forces are easily broken. This type of behavior is acceptable in our formulation, but is less desirable than the one depicted in FIGS. 10 to 12. When the curves are almost linear (the lower curve of FIG. 13), this means that we are dealing with a liquid with Newtonian behavior, the latter not being convenient either for our formulation.

Example 17

In this example we show another embodiment of the invention, where there are encapsulated minerals.

Figure 14:
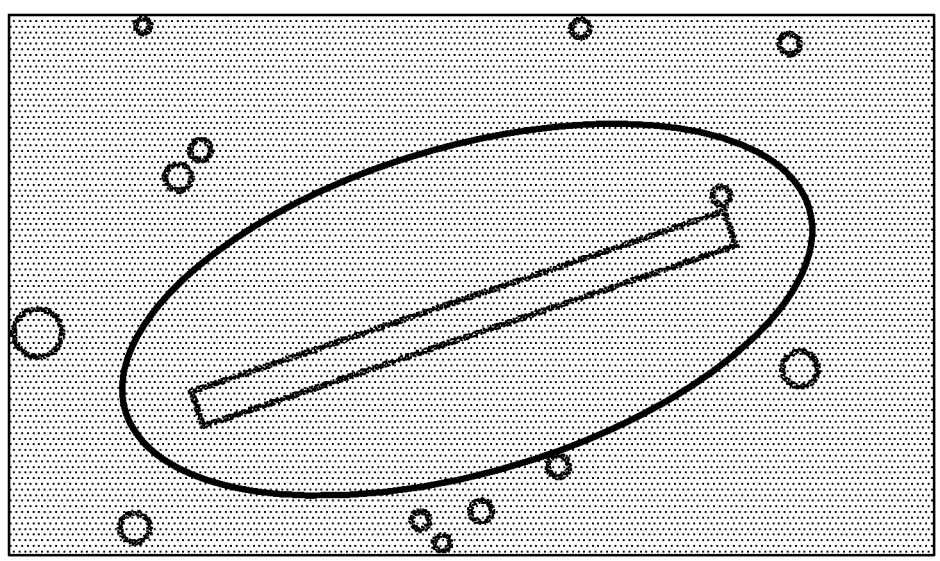
FIGS. 14 to 16 show microscopic views of the microcapsules and materials enclosed therein or in the continuous phase.

In the microphotograph (FIG. 14) we can appreciate the inclusion of inorganic minerals inside the core of a microcapsule. Selenium (from a suitable yeast culture) and zinc citrate have been added. It is clearly shown (ovale and arrow) a crystal of zinc citrate formed in the oil phase, at the same time that we observe the effect of multiencapsulation, where the small particles around are authentic microcapsules enclosed inside the bigger microcapsule that contains the crystals.

Example 18

In the present example we show two different types of microcapsules.

Figure 15:
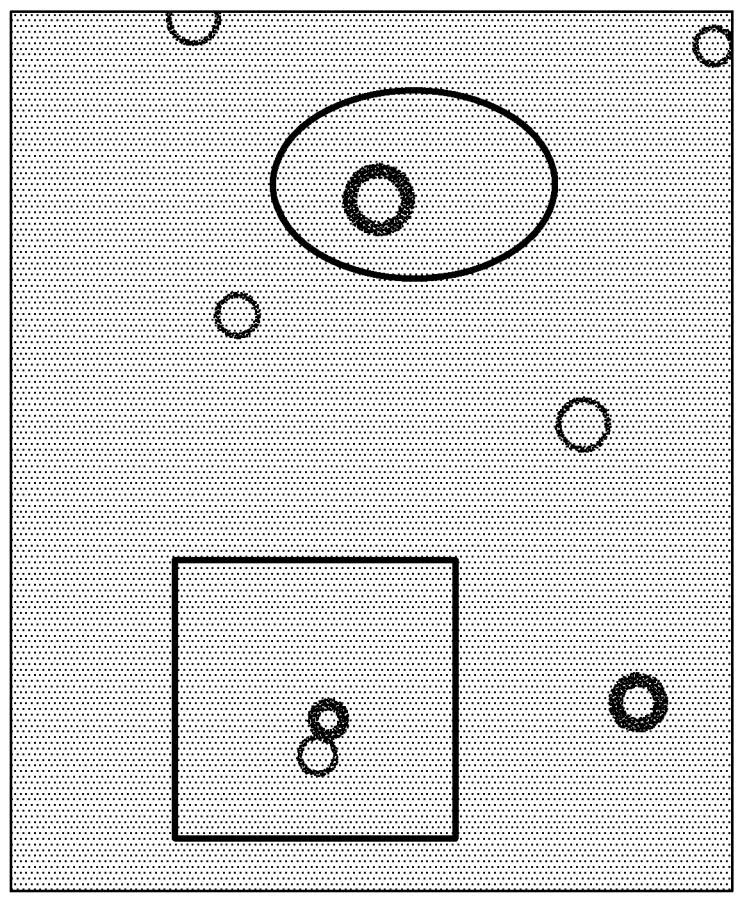
Figure 16:
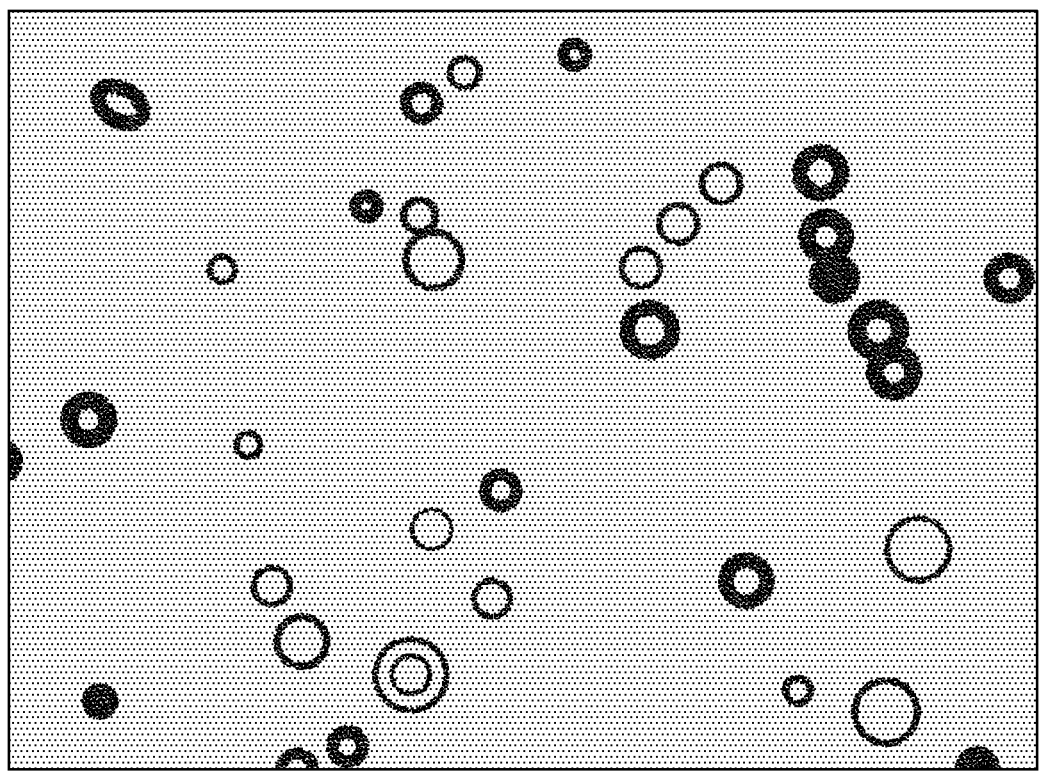
Figure 17:
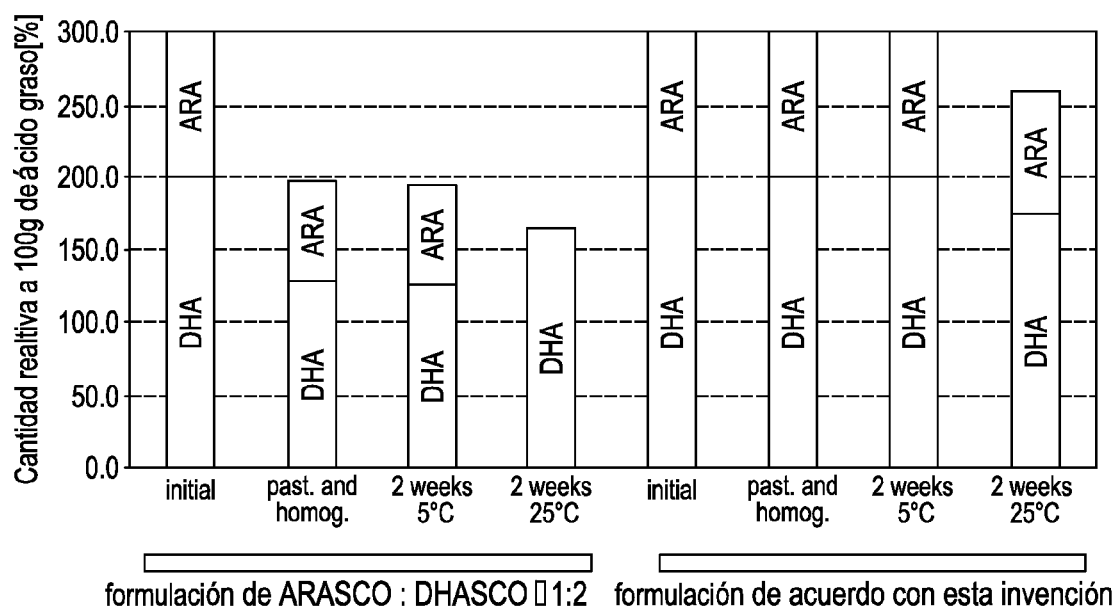
FIG. 17 represents the comparison of the temperature and shelf stability of omega 3 and omega 6 when microencapsulated as described in our invention (examples) vs. commercial "ready to add" omega-3 and omega-6 commercially available, showing a uncontestable better performance regarding stability of our microcapsules compared one the commercial product, in the standard conditions of the trial
Figure 18:
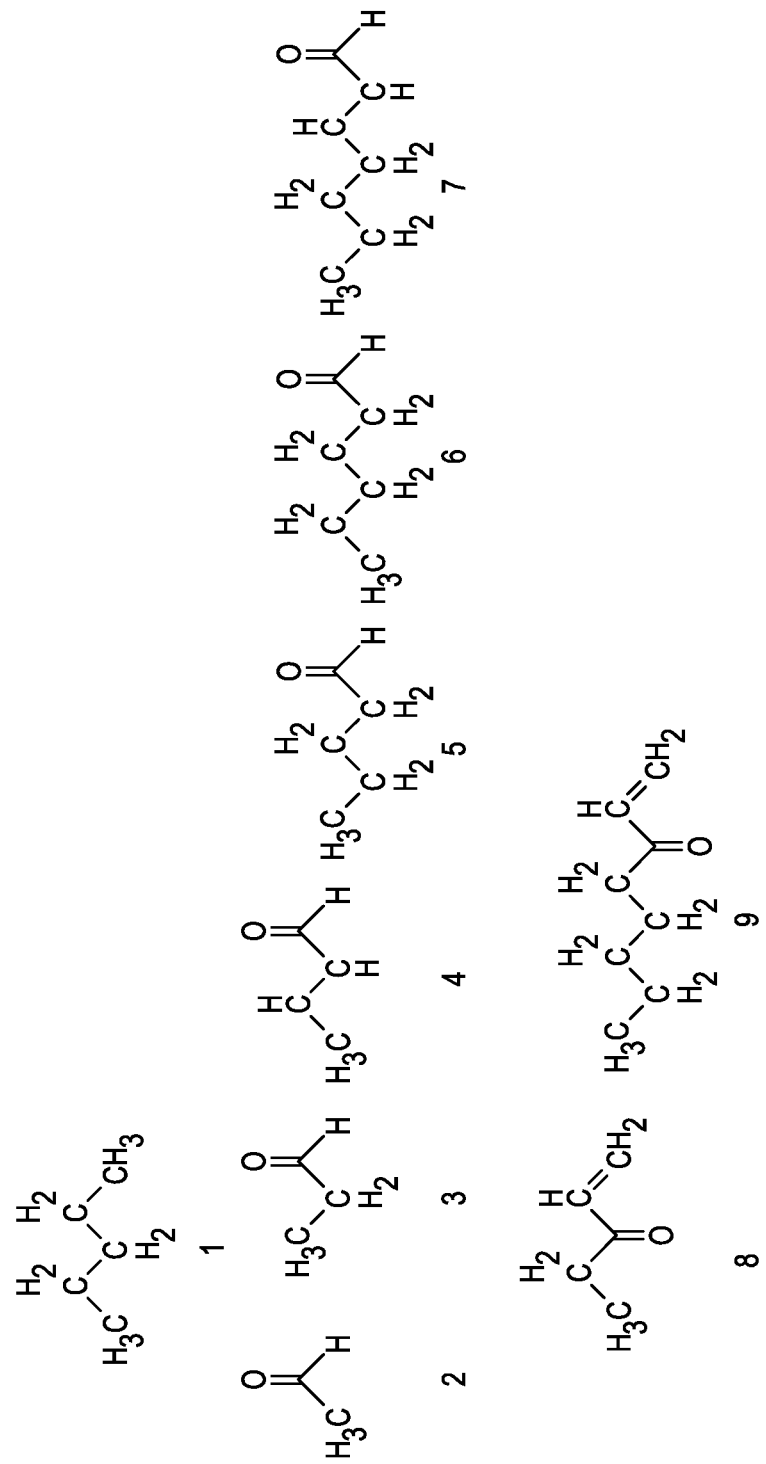
FIG. 18 shows typical and well described in the literature off-flavors and toxic and/or carcinogenic substances that appear when foodstuffs containing not well-protected UFAs are submitted to industrial processing or long storage.
Figure 19:
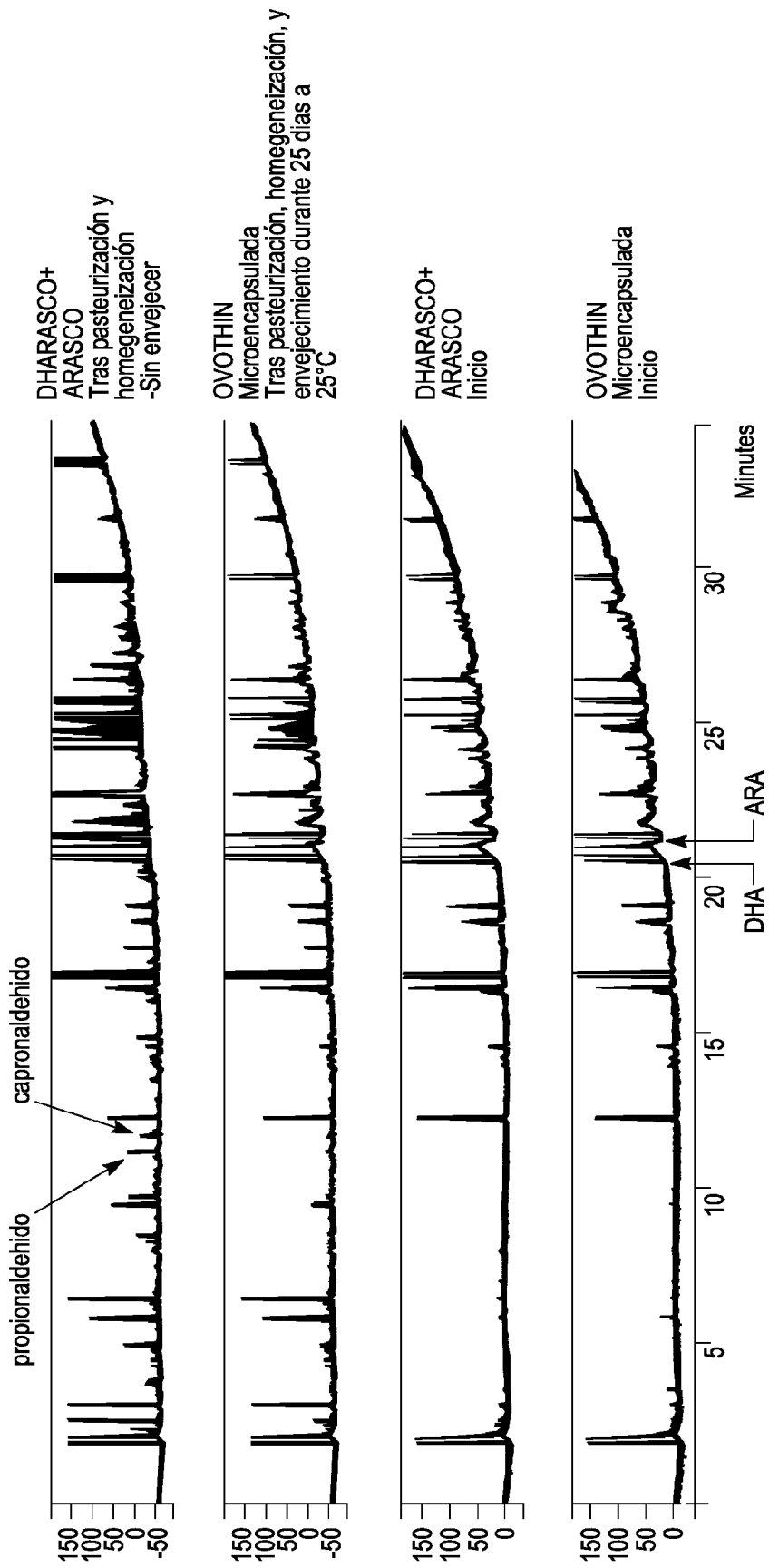
FIG. 19 shows the appearance of some of the compounds shown in FIG. 18 in non-microencapsulated foodstuffs containing omega-3 and omega-6 fatty acids, measured by gas chromatography and mass spectrometry and flame ionization detection.

In the microphotograph (FIG. 15), we appreciate single microcapsules (inside the rectangle) and also a microcapsule with more microcapsules inside (inside the oval). The adjustment of the light and focusing must be done in such a way the two compared types of microcapsules are at the same distance from the objective. Then, a big difference in the refraction of the light shows the degree of microencapsulation.

The invention claimed is:

1. Microcapsules, characterized in that:
    (a) each of the microcapsules having a wall containing an inner content of the microcapsules,
    (b) the wall of each of the microcapsules is formed by at least two polymerized hydrocolloids,
    (c) the inner content of the microcapsules consists in a first emulsion of water in oil and first inner microcapsules suspended in the first emulsion,
    (d) the average particle size of each of the microcapsules is 1-10 µm,
    (e) at least one biologically active ingredient is present in at least a discontinuous oil phase and/or in a discontinuous water phase in the microcapsules,
    (f) the first inner microcapsules each having a wall formed by the at least two polymerized hydrocolloids, and
    (g) the inner content of the first inner microcapsules each comprising a second emulsion of water in oil.

2. Microcapsules according to claim 1, characterized in that the microcapsules contain at least one biologically active compound originated by the group of organisms: *Medicago sativa, Pimenal officinalis, Hibiscus abelmoschus, Angelica archangelica, Galipea officinalis, Pimpinella anisum, Ferula foetida, Ferula asafetida, Melissa officinalis, Myroxylon pereirae, Ocimum basilicum, Pimenta acris, Citrus aurantium bergamia, Prunus amygdalus, Citrus aurantium, Citrus aurantium amara, Piper nigrum, Prunus spinosa, Aniba rosaeodora, Camelia oleifera, Camelia sinensis, Carum carvi, Elettaria cardamomum, Ceratonia siliqua, Daucus carota, Dacus carota sativa, Cascarilla, Apium graveolens, Anthemis nobilis, Matricaria chamomilla, Anthemis nobilis, Anthriscus cerefolium, Cichorium intybus, Cinnamomum spp., Cinnamomum zeylanicum, Cymbopogon nardus, Salvia sclarea, Trifolium pratense, Theobroma cacao, Coffea arabica, Coriandrium sativum, Cuminum cyminum, Taraxacum officinale, Sambucus nigra,* Edelweiss, *Helichrysum italicum, Foeniculum vulgare, Trigonella foenumgraecum, Arabidopsis spp., Zingiber officinale, Citrus grandis, Psidium guajava, Humulus lupus, Marrubium vulgare, Monarda punctata, Hyssopus officinals, Jasminum officinale, Jasminum grandiflorum, Juniperus* spp. *Juniperus comunis, Eucaliptus officinalis, Cola acuminata, Laurus nobilis, Lavandula* spp.,*Lavandula hybrida, Taxus baccata, Citrus medica limonum, Myristica fragans, Marjorana hortensis, Thymus* spp., *Thymus officinalis, Thymus mastichina, Ilex paraguarensis, Chamomilla recutita, Saccharum officinarum, Myristica fragans, Allium cepa, Citrus aurantium dulcis, Carum petroselinum, Mentha pulegium, Mentha piperita, Pimenta officinalis, Chimaphila umbellate, Punica granatum, Pelargonium* spp., *Pel-* argonium graveolens, Rosmarinus officinalis, Crocus sativus, Salvia spp., Salvia officinalis, Mentha spicata, Mentha viridis, Satureia hortensis, Satureja hortensis, Origanum majorana, Tamarindus indica, Citrus reticulata, Artemisia dracunculus, Thea sinensis, Thymus vulgaris, Polianthes tuberosa, Curcuma longa, Prunus serotina, Thymus serpillum, Satureja Montana, Cananga odorata, Curcuma zedoaria, Plantago major, Adansonia digitata, Ananas comosus, Artocarpus altilis, Carica papaya, Lycopersicon esculentum, Cephalophus spp., Vaccinium myrtillus, Thymus aragonensis, Thymus spp., Citrus aurantiifolia, Citrus paradisi, Cucumis melo, Cucurbita spp., Vitis spp., Vitis vinifera, Mangifera indica, Lamiaceae (Coleus, Hedeoma, Hyptis, Leonurus, Leucas, Lycopus, Marrubium, Mentha, Monarda, Perilla, Prunella, Salvia, Stachys, Teucrium, Thymus), Cannabis spp., Digitalis lanata, Adonis vernalis, Aesculus hippocastanum, Frazinus rhychophylla, Agrimonia supatoria, Rauvolfia sepentina, Andrographis paniculata, Areca catechu, Atropa belladonna, Berberis vulgaris, Ardisia japonica, Betula alba, Ananas comosus, Camellia sinensis, Cinnamomum camphora, Camptotheca acuminata, Potentilla fragarioides, Erythroxylum coca, Papaver somniferum, Colchicum autumnale, Claviceps purpurea, Digitalis purpurea, Digitalis lanata, Glaucium flavum, Gossypium spp., Hyoscyamus niger, Camptotheca acuminata, Piper methysticum, Lobelia inflata, Crotalaria sessiliflora, Nicotiana tabacum, Physostigma venenosum, Ephedra sinica, Cinchona ledgeriana, Rhododendron molle, Datura spp., Taxus brevifolia, Strychnos nux-vomica, Stevia rebaudiana, Valeriana officinalis, Pausinystalia yohimbe, Ephedra spp., Crataegus oxyacantha, Hamamelis virginiana, Hydrastis Canadensis, Hypericum perforatum, Potentilla erectra, Ledum palustre, Salvia officinalis, Chamomilla recutita, Arctostaphylos uva, Eucommia ulmoides, Mytilus galloprovincialis, Diplazium esculentum, Manihot utillissima, Sauropous androgynus, Terminalia arjuna, Iberis amara, Crataegus spp., Arbutus unedo, Cynara scolymus, Amaranthus caudatus, Alchornea laxiflora, Alpinia officinarum, Xanthophyllomyces dendrorhous, Crataegus monogyna, Taxus yunnanensis, Bacopa monniera, Cistus albidus, Ocimum basilicum, Rosmarinus officinalis, Thymus vulgaris, Bixa orellana, Centella asiatica, Urtica dioica, Agrocybe aegerita, Crataegus laevigata, Satureja hortensis, Crocus sativus, Coccinia indica, Brugia malayi, Rubus spp., Silybum marianum, Cannabis sativa, Hypericum perforatum, Rhus coriaria, Olea europaea, Cyclopia intermedia, Ginkgo biloba, Lentinus lepideus, Pseudomonas putida, Sargassum micracanthum, Pinus radiata, Pinus spp., Phaseoulus mungo, Cicer arietinum, Vigna sinensis, Phaseolus aureus, Dolichos lablab, Cajanus cajan, Vicia faba, Dolichos biflorus, Phaseolus lunatus, Phaseolus aconitifolius, Pisum sativum, Psophocarpus tetragonolobus, Arachis hypoagea, Brassica spp., Brassica campestris, Brassica napus, Valeriana officinalis, Echinacea purpurea, Echinacea pallida, Echinacea angustifolia, Glcyrrhiza glabra, Seronea repens, Vaccinium macrocarpon, Tancetum parthenuum, Tancetum parthenuum, Vaccinium macrocarpon, cereals, seed fruits, silvestre bays, leguminosae, green tea, black tea and microorganisms able to produce long-chained unsaturated fatty acids.

3. Microcapsules according to claim 1, characterized in that the microcapsules contain at least one of the biologically active materials selected from (A) and/or (B) in all their stereochemical and isomeric variations:

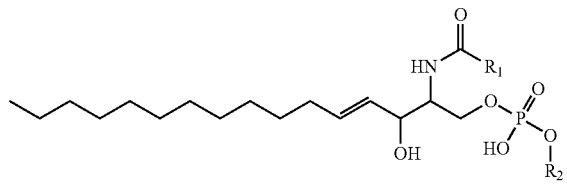

Compound(s) A wherein,
$R_1$ is an omega-3 or omega-6 fatty acid esterified
$R_2$ is an omega-3 or omega-6 fatty acid esterified

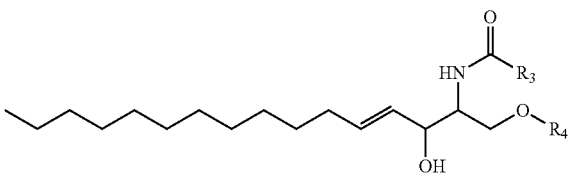

Compound(s) B $R_3$ is an omega-3 or omega-6 fatty acid esterified
$R_4$ is an omega-3 or omega-6 fatty acid esterified.

4. Microcapsules according to claim 1 characterized in that they contain at least one unsaturated long-chain fatty acid of at least 6 carbon atoms, in any isomeric and/or stereochemical configuration, as well as any esters, ethers, glycerides, phospholipids, and sphingolipids derivatives thereof.

5. Microcapsules according to claim 1 characterized in that they contain unsaturated fatty acids with a carbon chain of at least 6 carbon atoms that come from the following groups of natural sources or from genetically modified organisms of the following natural sources:

(a) vegetable origin: Boraginaceae, (Borago spp., Borago officinalis); Linaceae (Linum usitatissimum, Linum arvense, Linum sativum); Onograceae (Oenothera Biennis); Grossulariaceae\ (Ribes nigrum), Zea Mais, Gossypium hirsutum, Carthamus tinctorius, Glycine max. Boraginaceae, (Borago spp., Borago officinalis), Linaceae (Linum usitatissimum, Linum arvense, Linum sativum), Onograceae (Oenothera biennis), Grossulariaceae (Ribes nigrum), Zea Mais, Gossypium hirsutum, Carthamus tinctorius, Glycine max;

(b) algae origin: Graciliariceae (Gracilaria spp.), Gigartinaceae (Iridaea spp.), Kallymeniaceae (Callopyllis varicgata), Durvillaceae (Durvillaea antartica), Solieriaceae (Euchema cottoni), Gelidiaceae (Gelidium spp,), Lossoniaceae (Lesonia nigrescens), Gigantinaceae (Gigartina spp.), Lessoniaceae (Macrocystis spp.), Bangiaceae (Porphyra spp.), Crypthecodinium spp.;

(c) animal origin: Engaulidae (Lycengraulis olidus), Clupeidae (Sardina pilchardus), Scomberesocidae (Scomberesox saurus scombroides), Berycidae (Beryx splendens), Engraulidae (Engraulis ringens), Ophichthyidae (Ophichthus spp.), Serranidae (Hemilutjanus macrophthalmus), Scombridae (Thunnus spp., en especial, Thunnus albacares, Thunnus alalunga, Thunnus obesus, Sarda spp., Sarda chiliensis, Scomber japonicus peruanus)), Sciaenidae (Cynoscion analis), Carcharhinidae (Prionace glauca), Normanichthyidae (Normanichthys crockeri), Percichthyidae (Polyprion oxygeneios), Nototheniidae (Dissostichus eleginoides), Apogonidae (*Epigonus crassicaudus*), Branchiostegidae (*Prolatilus jugularis*), Normanichthyidae (*Normanichthys crockeri*), Percichthyidae (*Polyprion oxygeneios*), Notothemiidae (*Bacalao de profundidad*), Apogonidae (*Epigonus crassicaudus*), Branchiostegidae (*Prolatilus jugularis*), Cheilodactylidae (*Cheilodactylus gavi*), Gadidae (*Salilota australis*), Pomadasvidae, Scorpaenidae, Serranidae, Cyprinidae, Monacanthidae, Centrolophidae, Ophidiidae, Coryphaenidae, Channichthydae, Sciaenidae, Aplodactylidae, Carangidae (*Trachurus symetricus murphyi*), Bothidae (*Paralichthys microps*), Mugilidae, Priacathidae, Merlucciidae (*Merluccius gayi gayi, Merluccius australis*), Macruronidae (*Macruronus magellanicus*), Gadidae (*Micromesistius australis*), Girellidae, Trachichthvidae, Carangidae, Kvphosidae, Callorhvnchidae, Labridae, Macrouridae, Atherinidae, Gobiesocidae, Alopiidae, Galaxiidae, Rajidae, Bramidae, Carangidae, Nototheniidae, Scianidae, Mugiloidae, Salmonidae (*Salmo* spp., *Salmo salar, Oncorhynchus* spp., *Oncorhynchus kisutch, Oncorhynchus mykiss, Oncorhynchus tshawytscha*), Clupeidae (*Sardinops* spp., *Sardinops sagax, Clupea bentincki*), Pomadasvidae, Gempvlidae, Lamnidae (*Isurus* spp., *Isurus oxyrinchus*), Triakidae, Clinidae, Scophthalmidae, and more preferably Atlantic mackerel, *Engraulis encrasicholus, Pomatomus saltatrix, Sarda sarda, Sardina pilchardus, Brevoortia tyrannus, Brevoortia patronus, Chloroscombrus chrysurus, Auxis thazard, Scomber scombrus, Scomber japonicus, Alosa aestivalis, Clupea harengus, Etrumeus teres, Argentina silus, Ictalurus punctatus*; and (d) microbial origin: *Saccharomices cerevisiae, Escherichia coli, Schizochytrium* spp., *Thraustochytrium aurcum, Thraustochytrium roscum, Thraustochytrium striatum, Mortiriella* spp., *Phytium* spp., *Aspergillus* spp. *Aspergillus nidulans, Aspergillus sydowi, Fusarium* spp., *Fusarium equiseti, Fusarium oxysporum.*

6. Microcapsules produced according to claim 1, characterized in that the microcapsules are stable and the microcapsule's wall does not open at pH higher than 3.5.

7. Microcapsules according to claim 1 characterized in that they contain in the oil phase at least one compound selected from: fish oil, flax oil, omega-3 and/or omega-6 and/or omega-9 fatty acids, conjugated linoleic acids, terpenoids, carotenoids, tocotrienols, flavonoids, hormones, antioxidants.

8. Microcapsules according to claim 1 characterized in that they contain in the water phase at least one compound selected from:
polyphenols, proantocyanidins, anthocyans, alpha-lipoic acid, coenzyme Q-10 aminoacids, peptides, enzymes, enzyme inhibitors, minerals, oligoelements, green tea extracts, rosemary extracts, *Thymus* spp. extracts, raspberry extracts, *Mentha piperita* extracts, iron, selenium, magnesium, antioxidants, hormones, probiotic bacteria or fungi or yeasts.

9. Microcapsules according to claim 1 characterized in that they contain at least one biologically active material at least a biologically active material selected from the groups;

(a) flavonoids, anthocyianidins, pro-anthocyanidins, oligomeric proanthocyanidins, isoflavones, chalcones, catechin, epihatechin, epicatechin gallate, epigallocatechin, epigallocatechin gallate, eriodtrin, narirutin, rutin, naringin, myricitrin, hesperidin, myricetin, eriodictyol, fisetin, quercetin, naringenin, luteolin, hesperitin, kaempferol, isorhamnetin, apigenin, rhamnetin, galangin, quercitrin, diosmetin, taxifolin, galandin, biochanin A, genistein, eriodictyol, chrysin, hydroxytyrosol, oleuropein, glabridine, licochalcone, daidzein, matairesinol, secoisolariciresinol, enterodiol, enterolactone, equol, desmethylangolensin, luteoferol, luteolinidin, apiferol, apigenidin, leucocyanidin, taxifolin, pelargonidin;

(b) phenolic acids in general and esters, glycosides, rutinosides and amines thereof, gallic, sinapic, syringic, caffeic, chlorogenic, ferulic, procatechuic, vanillic, hydroxycinnamic, and coumaric acids, guaiacol, cresol, 4-ethylphenol, 4-vinylguaicol, eugenol, tannins, ellagiotannins, gallotannins;

(c) esctructurally combined amides comprising hydroxycinnamic acids and anthranilic acids (avenanthramides), avenasterol, long-chain fatty acids or alcohols, indoleamines, melatonin, inulin, glutation;

(d) terpenoids, monoterpenes, diterpenes, sesquiterpenes, triterpenes, tetraterpenes, carotenoids, alfa-carotene, phytoene, cyclo-artenol, betacarotene, ionone, zeaxanthin, capsanthin, astaxanthin, canthaxantin, (e) violaxanthin, mutatoxanthin, luteoxanthin, auroxanthin, neoxanthin, apocarotinal, xanthophylls;

(f) butylhydroxyanisol, 2,6-di-tert-butylhydroxytoluene, tert-butylhydroquinone, 2,6-di-tert-butylhydroquinone, 2,6-diterbutyl-4-hydroxymethylphenol, 2,4,5-trihidroxibutyro phenone, alpha, beta, gamma and delta tocopherols, alpha, beta, gamma and delta tocotrienols, alpha, beta, gamma and delta tocochromanols;

(g) alpha-lipoic acid, coenzyme Q-10, vitamins, aminoacids, L-arginine, cistine, cisteine, oligopeptides, peptides, carnosine, carnitine, glutathione, enzymes; enzyme inhibitors, phenolases or oxigenases or lipooxigenases or lipase inhibitors;

(h) minerals and oligoelements, selenium, zinc, magnesium.

10. Microcapsules according to claim 1 characterized in that the microcapsules contain at least one biologically active compound obtained from the following group of organisms:
*Medicago sativa, Pimenal officinalis, Hibiscus abelmoschus, Angelica archengelica, Galipea officinalis, Pimpinella anisum, Ferule foetida, Ferula asafetida, Melissa officinalis, Myroxylon pereirae, Ocimum basillicum, Pimenta acris, Citrus aurantium bergamia, Prunus amygdalus, Citrus aurantium, Citrus aurantium amara, Piper nigrum, Prunus spinosa, Anibe rosaeodora, Camelia oleifera, Camelia sinensis, Carum carni, Elettaria cardamomum, Ceratonia siliqua, Daucus carota, Dacus carota sativa, Cascarilla, Apium graveolens, Anthemis nobilis, Matricaria chamomilia, Anthemis nobilis, Anthriscus cerefolium, Cichorium intybus, Cinnamomum* spp., *Cinnamomum zeylanicum, Cymbopogon nardus, Salvia sciarea, Trifolium pratense, Theobroma cacao, Coffea arabica, Coriandrium sativum, Cumlnum cyminum, Taraxacum officinale, Sambucus nigra,* Edelweiss, *Helichrysum italicum, Foeniculum vulgare, Trigonella foenumgraecum, Arabidopsis* spp., *Zingiber officinale, Citrus grandis, Psidium guajava, Humulus lupus, Marrubium vulgare, Monarda punctata, Hyssopus officinals, Jasminum officinale, Jasminum grandiflorum, Juniperus* spp., *Juniperus comunis, Eucaliptus officinalis, Cola acuminata, Laurus nobilis, Lavandula* spp., *Lavanduia hybrida, Taxus baccata, Citrus medica limonum, Myristica fragans, Marjorana hortensis, Thymus* spp., *Thymus officinalis, Thymus mastichina, Ilex paraguarensis, Chamomilla recutita, Saccharum officinarum, Myristica fragans, Allium cepa, Citrus aurantium duicis, Carum petroselinum, Mentha pulegium,*

Mentha piperita, Pimenta officinalis, Chimaphiia umbellate, Punica granatum, Pelargonium spp., Pelargonium graveolens, Rosmarinus officinalis, Crocus sativus, Salvia spp., Salvia officinalis, Mentha spicata, Mentha viridis, Satureia hortensis, Satureja hortensis, Origanum majorana, Tamarindus indica, Citrus reticulata, Artemisia dracunculus, Thea sinensis, Thymus vulgaris, Polianthes tuberosa, Curcuma longa, Prunus serotina, Thymus serpillum, Satureja montana, Cananga odorata, Curcuma zedoaria, Plantago major, Adansonia digitata, Ananas comosus, Artocarpus altilis, Carica papaya, Lycopersicon esculentum, Cephalophus spp., Vaccinium myrtillus, Thymus aragonensis, Thymus spp., Citrus aurantiifolia, Citrus paradisi, Cucumis melo, Cucurbita spp., Vitis spp., Vitis vinifera, Mangifera indica, Lamiaceae, Coleus ssp., Hedeoma ssp., Hyptis ssp., Leonurus spp., Leucas ssp., Lycopus, ssp., Marrubium spp., Mentha spp., Monarda spp., Periila spp., Prunella spp., Salvia spp., Stachys spp., Teucrium spp., Thymus spp., Cannabis spp., Digitalis lanata, Adonis vernalis, Aesculus hippocastanum, rrazinus rhychophylla, Agrimonia supatoria, Rauvolfia sepentina, Andrographis panicuiata, Areca catechu, Atropa belladonna, Berberis vulgaris, Ardisia japonica, Betula alba, Ananas comosus, Camellia sinensis, Cinnamomum camphora, Camptotheca acuminata, Potentilla fragarioides, Erythroxylum coca, Papaver somniferum, Colchicum autumnale, Claviceps purpurea, Digitalis purpurea, Digitalis lanata, Glaucium flavum, Papaver somniferum, Gossypium spp., Hyoscyamus niger, Camptotheca acuminata, Piper methysticum, Lobelia inflata, Crotalaria sessiliflora, Nicotiana tabacum, Physostigma venenosum, Ephedra sinica, Cinchona ledgeriana, Rhododendron molle, Datura spp., Taxus brevifolia, Strychnos nux-vomica, Stevia rebaudiana, Valeriana officinalis, Pausinystalia yohimbe, Ephedra spp., Crataegus oxyacantha, Hamamelis virginiana, Hydrastis canadensis, Hypericum perforatum, Potentilla erectra, Ledum palustre, Salvia officinalis, Chamomilla recutita, Arctostaphylos uva, Eucommia ulmoides, Mytilus galioprovincialis, Dipiazium esculentum, Manihot utillissima, Sauropous androgynus, Terminalia arjuna, Iberis amara, Crataegus spp., Arbutus unedo, Cynara scolymus, Amaranthus caudatus, Alchornea laxiflora, Alpinia officinarum, Xanthophyilomyces dendrorhous, Crataegus monogyna, Taxus yunnanensis, Bacopa monniera, Cistus albidus, Ocimum basilicum, Thymus vulgaris, Bixa orellana, Centella asiatica, Urtica dioica, Agrocybe aegerita, Crataegus laevigata, Satureja hortensis, Crocus sativus, Coccinia indica, Brugia malayi, Rubus spp., Silybum marianum, Cannabis spp., Cannabis sativa, Hypericum perforatum, Rhus coriaria, Olea europaea, Cyclopia intermedia, Ginkgo biloba, Lentinus lepideus, Pseudomonas putida, sargassum micracanthum, Pinus radiata, Pinus spp., Phaseoulus mungo, Cicer arietinum, Vigna sinensis, Phaseolus aureus, Dolichos lablab, Cajanus cajan, Vicia faba, Dolichos biflorus, Phaseolus lunatus, Phaseolus aconitifolius, Pisum sativum, Psophocarpus tetragonolobus, Arachis hypoagea, Brassica spp., Brassica campestris, Brassica napus, Valeriana officinalis, Echinacea purpurea, Echinacea pallida, Echinacea angustifolia, Glycyrrhiza glabra, Seronea repens, Vaccinium macrocarpon, Tancetum parthenuum, Vaccinium macrocarpon, cereals, seed fruits, silvestre bays, leguminosae, green tea, black tea, microorganisms able to produce long-chained unsaturated fatty acids, Lactobacillus casci, L. acidophillus, L. rhamnosus, L. paracasei, L. gasseri, L. fermentum, L. plantarum, L. salivarius, L. crispatus, L. bulgaricus, L. fermentum, L. reuteri, Bifidobacterium infantis, B. bifidum, Streptococcus termophilus, S. bovis Enterococcus durans, E. faecalis, E. Gallinarum, Esherichia coli, Propionibacterium freudenreicheii, and genetically modified bacteria or fungi or yeasts having inserted genes of probiotic bacteria, Saccharomyces cerevisiae, Kluyveromices marxianus, Rhodotorula rubra, Orobolomvces puniceus, Aureobasidium pullulans, Leucosporidium scotti.

11. Microcapsules according to claim 1 characterized in that they ontain at least one compound selected from the acids: arachidonic, sterad onic, eicosapentenoic, docosahexenoic, docosapentenoic, linoieic, conjugated linoleic, inolenic, gamma•linolenic, alpha-linoleic, dihomogamma-linolenic, leic acid; in any isomeric and/or stereochemical configuration, as well as any ester, ether, glyceride, phospholipid, sphingolipid derivatives thereof.

12. Microcapsules according to claim 1 characterized in that they contain a combination of compounds selected from: omega-3, omega-6, omega-9 fatty acids and cerebrosides.

13. Microcapsules according to claim 1 characterized in that they contain a mixture of omega-3 and omega-6 fatty acids in a ratio 0.5-10.0, and contain cerebrosides in a percentage of 0.005%-1% with respect to the weight of omega-3 plus omega-6 fatty acids.

14. Microcapsules according to claim 1 characterized in that they release the biologically active material(s) by at least a factor belonging to the group; pH, temperature, ionic force, osmosis, volatilization or presence of chemicals or enzymes that dissolve the microcapsules' wall.

15. Microcapsules according to claim 1 characterized in that the inner content of one or more of the first inner microcapsules comprises second inner microcapsules suspended in the second emulsion.

16. Microcapsules according to claim 15 characterized in that the microcapsules are multi-microcapsules having up to 5 degrees of multi-microencapsulation, and wherein each degree of multi-microencapsulation comprises a first microcapsule suspended in an emulsion of water in oil of a second microcapsule.

* * * * *